US012746402B2

(12) United States Patent
Briscoe et al.

(10) Patent No.: US 12,746,402 B2
(45) **Date of Patent: *Sep. 29, 2026**

(54) WEARABLE CARDIOVERTER DEFIBRILLATOR (WCD) SYSTEM LOGGING EVENTS AND BROADCASTING STATE CHANGES AND SYSTEM STATUS INFORMATION TO EXTERNAL CLIENTS

(71) Applicant: West Affum Holdings DAC, Dublin (IE)

(72) Inventors: Megan Eileen Briscoe, Bothell, WA (US); Erick Michael Roane, Kirkland, WA (US); Robert Curtis Birkner, Woodinville, WA (US); David Peter Finch, Bothell, WA (US)

(73) Assignee: West Affum Holdings DAC, Dublin (IE)

( * ) Notice: Subject to any disclaimer, the term of this patent is extended or adjusted under 35 U.S.C. 154(b) by 786 days.

This patent is subject to a terminal disclaimer.

(21) Appl. No.: 18/087,342

(22) Filed: Dec. 22, 2022

(65) Prior Publication Data

US 2023/0130416 A1 Apr. 27, 2023

Related U.S. Application Data

(63) Continuation of application No. 16/396,415, filed on Apr. 26, 2019, now Pat. No. 11,534,615.

(Continued)

(51) Int. Cl.

*A61N 1/39* (2006.01)
*A61B 5/00* (2006.01)

(Continued)

(52) U.S. Cl.

CPC .............. *A61N 1/3904* (2017.08); *A61B 5/01* (2013.01); *A61B 5/318* (2021.01); *A61B 5/721* (2013.01);

(Continued)

(58) Field of Classification Search

CPC ...... A61N 1/3904; A61N 1/3925; A61B 5/01; A61B 5/318; A61B 5/721; A61B 5/7221; A61B 5/7405; A61B 5/7455; A61B 5/746

See application file for complete search history.

(56) References Cited

U.S. PATENT DOCUMENTS

| | | | |
|---|---|---|---|
| 3,724,455 | A | 4/1973 | Unger |
| 4,583,524 | A | 4/1986 | Hutchins |

(Continued)

FOREIGN PATENT DOCUMENTS

| | | | |
|---|---|---|---|
| WO | 9839061 | A2 | 9/1998 |

OTHER PUBLICATIONS

Heartstart MRx and XL AED Algorithm-Application Note, Jul. 2001, Edition 2 Philips Healthcare, USA.

(Continued)

*Primary Examiner* — Kristina N Junge

(74) *Attorney, Agent, or Firm* — Seed Intellectual Property Law Group LLP

(57) ABSTRACT

Methods, apparatus, and systems relating to a Wearable Cardioverter Defibrillator (WCD) system capable of logging event data and/or broadcasting state changes and/or system status information to external clients are described. In an embodiment, a processor stores data corresponding to one or more event markers in memory in response to occurrence of an event. Occurrence of the event is detected based at least in part on detection of one or more parameters by one or more sensors or a signal to be generated by one or more of electrodes of the WCD system. A communication device transmits at least a portion of the stored data to a remote device. A patient condition or a WCD system condition can (Continued)

SAMPLE COMPONENTS OF EXTERNAL DEFIBRILLATOR then be detected based at least in part on analysis of the stored data and/or the transmitted portion of the stored data. Other embodiments are also disclosed and/or claimed.

17 Claims, 8 Drawing Sheets

Related U.S. Application Data

(60) Provisional application No. 62/662,892, filed on Apr. 26, 2018.

(51) Int. Cl.
*A61B 5/01* (2006.01)
*A61B 5/318* (2021.01)

(52) U.S. Cl.
CPC .......... *A61B 5/7221* (2013.01); *A61B 5/7405* (2013.01); *A61B 5/7455* (2013.01); *A61B 5/746* (2013.01); *A61N 1/3925* (2013.01)

(56) References Cited

U.S. PATENT DOCUMENTS

| | | | |
|---|---|---|---|
| 4,619,265 | A | 10/1986 | Morgan et al. |
| 4,928,690 | A | 5/1990 | Heilman et al. |
| 4,955,381 | A | 9/1990 | Way et al. |
| 5,078,134 | A | 1/1992 | Heilman et al. |
| 5,228,449 | A | 7/1993 | Christ et al. |
| 5,348,008 | A | 9/1994 | Bomnn et al. |
| 5,353,793 | A | 10/1994 | Bomn |
| RE34,800 | E | 11/1994 | Hutchins |
| 5,394,892 | A | 3/1995 | Kenny et al. |
| 5,405,362 | A | 4/1995 | Kramer et al. |
| 5,474,574 | A | 12/1995 | Payne et al. |
| 5,662,690 | A | 9/1997 | Cole et al. |
| 5,782,878 | A | 7/1998 | Morgan et al. |
| 5,792,204 | A | 8/1998 | Snell |
| 5,902,249 | A | 5/1999 | Lyster |
| 5,913,685 | A | 6/1999 | Hutchins |
| 5,944,669 | A | 8/1999 | Kaib |
| 6,047,203 | A | 4/2000 | Sackner et al. |
| 6,065,154 | A | 5/2000 | Hulings et al. |
| 6,108,197 | A | 8/2000 | Janik |
| 6,148,233 | A | 11/2000 | Owen et al. |
| 6,201,992 | B1 | 3/2001 | Freeman |
| 6,263,238 | B1 | 7/2001 | Brewer et al. |
| 6,287,328 | B1 | 9/2001 | Snyder et al. |
| 6,304,780 | B1 | 10/2001 | Owen et al. |
| 6,319,011 | B1 | 11/2001 | Motti et al. |
| 6,334,070 | B1 | 12/2001 | Nova et al. |
| 6,356,785 | B1 | 3/2002 | Snyder et al. |
| 6,427,083 | B1 | 7/2002 | Owen et al. |
| 6,529,875 | B1 | 3/2003 | Nakajima et al. |
| 6,546,285 | B1 | 4/2003 | Owen et al. |
| 6,671,545 | B2 | 12/2003 | Fincke |
| 6,681,003 | B2 | 1/2004 | Linder et al. |
| 6,762,917 | B1 | 7/2004 | Verbiest et al. |
| 7,065,401 | B2 | 6/2006 | Worden |
| 7,559,902 | B2 | 7/2009 | Ting et al. |
| 7,865,238 | B2 | 1/2011 | Brink |
| 7,870,761 | B2 | 1/2011 | Valentine et al. |
| 7,974,689 | B2 | 7/2011 | Volpe et al. |
| 8,135,462 | B2 | 3/2012 | Owen et al. |
| 8,140,154 | B2 | 3/2012 | Donnelly et al. |
| 8,369,944 | B2 | 2/2013 | Macho et al. |
| 8,548,557 | B2 | 10/2013 | Garstka et al. |
| 8,615,295 | B2 | 12/2013 | Savage et al. |
| 8,644,925 | B2 | 2/2014 | Volpe et al. |
| 8,897,860 | B2 | 11/2014 | Volpe et al. |
| 8,904,214 | B2 | 12/2014 | Volpe et al. |
| 8,965,500 | B2 | 2/2015 | Macho et al. |
| 9,008,801 | B2 | 4/2015 | Kaib et al. |
| 9,089,685 | B2 | 7/2015 | Sullivan et al. |
| 9,131,901 | B2 | 9/2015 | Volpe et al. |
| 9,132,267 | B2 | 9/2015 | Kaib |
| 9,408,548 | B2 | 8/2016 | Volpe et al. |
| 9,454,219 | B2 | 9/2016 | Volpe et al. |
| 9,592,403 | B2 | 3/2017 | Sullivan |
| 10,159,415 | B2 | 12/2018 | Gopalakrishnan et al. |
| 11,160,990 | B1 | 11/2021 | Sullivan et al. |
| 2003/0158593 | A1 | 8/2003 | Heilman et al. |
| 2005/0107833 | A1 | 5/2005 | Freeman et al. |
| 2005/0107834 | A1 | 5/2005 | Freeman et al. |
| 2008/0312709 | A1 | 12/2008 | Volpe et al. |
| 2009/0005827 | A1 | 1/2009 | Weintraub et al. |
| 2009/0318779 | A1 | 12/2009 | Tran |
| 2010/0007413 | A1 | 1/2010 | Herleikson et al. |
| 2010/0298899 | A1 | 11/2010 | Donnelly et al. |
| 2011/0022105 | A9 | 1/2011 | Owen et al. |
| 2011/0288604 | A1 | 11/2011 | Kaib et al. |
| 2011/0288605 | A1 | 11/2011 | Kaib et al. |
| 2012/0092157 | A1 | 4/2012 | Tran |
| 2012/0112903 | A1 | 5/2012 | Kaib et al. |
| 2012/0144551 | A1 | 6/2012 | Guldalian |
| 2012/0150008 | A1 | 6/2012 | Kaib et al. |
| 2012/0158075 | A1 | 6/2012 | Kaib et al. |
| 2012/0191476 | A1 | 7/2012 | Reid et al. |
| 2012/0215076 | A1 | 8/2012 | Yang et al. |
| 2012/0265265 | A1 | 10/2012 | Razavi et al. |
| 2012/0283794 | A1 | 11/2012 | Kaib et al. |
| 2012/0293323 | A1 | 11/2012 | Kaib et al. |
| 2012/0302860 | A1 | 11/2012 | Volpe et al. |
| 2012/0310315 | A1 | 12/2012 | Savage et al. |
| 2012/0330109 | A1 | 12/2012 | Tran |
| 2013/0009783 | A1 | 1/2013 | Tran |
| 2013/0069780 | A1 | 3/2013 | Tran et al. |
| 2013/0072807 | A1 | 3/2013 | Tran |
| 2013/0085538 | A1 | 4/2013 | Volpe et al. |
| 2013/0172691 | A1 | 7/2013 | Tran |
| 2013/0178718 | A1 | 7/2013 | Tran et al. |
| 2013/0231711 | A1 | 9/2013 | Kaib |
| 2013/0245388 | A1 | 9/2013 | Rafferty et al. |
| 2013/0274565 | A1 | 10/2013 | Langer et al. |
| 2013/0317852 | A1 | 11/2013 | Worrell et al. |
| 2013/0325078 | A1 | 12/2013 | Whiting et al. |
| 2014/0025131 | A1 | 1/2014 | Sullivan et al. |
| 2014/0070957 | A1 | 3/2014 | Longinotti-Buitoni et al. |
| 2014/0121476 | A1 | 5/2014 | Tran et al. |
| 2014/0163425 | A1 | 6/2014 | Tran |
| 2014/0163663 | A1 | 6/2014 | Poddar et al. |
| 2014/0249429 | A1 | 9/2014 | Tran |
| 2014/0257047 | A1 | 9/2014 | Sillay et al. |
| 2014/0324112 | A1 | 10/2014 | Macho et al. |
| 2014/0378812 | A1 | 12/2014 | Saroka et al. |
| 2015/0039053 | A1 | 2/2015 | Kaib et al. |
| 2015/0165222 | A1 | 6/2015 | Oskin et al. |
| 2015/0182130 | A1 | 7/2015 | Utter |
| 2015/0186609 | A1 | 7/2015 | Utter, II |
| 2015/0328472 | A1 | 11/2015 | Sullivan et al. |
| 2015/0331996 | A1 | 11/2015 | Gustavson et al. |
| 2016/0004831 | A1 | 1/2016 | Carlson et al. |
| 2016/0074667 | A1 | 3/2016 | Sullivan et al. |
| 2016/0082277 | A1 | 3/2016 | Foshee, Jr. et al. |
| 2016/0217672 | A1 | 7/2016 | Yoon et al. |
| 2016/0360965 | A1 | 12/2016 | Tran |
| 2016/0367157 | A1 | 12/2016 | Blake et al. |
| 2017/0011210 | A1 | 1/2017 | Cheong et al. |
| 2017/0065823 | A1 | 3/2017 | Kaib et al. |
| 2017/0128735 | A1 | 5/2017 | Gustavson et al. |
| 2017/0181645 | A1 | 6/2017 | Mahalingam et al. |
| 2017/0181703 | A1* | 6/2017 | Kaib .................... A61N 1/3943 |
| 2017/0238812 | A1 | 8/2017 | Atlas |
| 2017/0279612 | A1 | 9/2017 | Liang et al. |
| 2017/0296056 | A1 | 10/2017 | Hresko et al. |
| 2017/0300653 | A1 | 10/2017 | Hresko et al. |
| 2017/0347886 | A1 | 12/2017 | Tran |
| 2017/0347894 | A1 | 12/2017 | Bhushan et al. |
| 2018/0093102 | A1 | 4/2018 | Sullivan et al. |
| 2018/0132081 | A1 | 5/2018 | Ulmansky et al. |
| 2018/0206783 | A1 | 7/2018 | Yoon et al. |
| 2018/0233016 | A1 | 8/2018 | Daniel et al. |
| 2018/0277255 | A1 | 9/2018 | Martin et al. |

(56) References Cited

U.S. PATENT DOCUMENTS

| | | | |
|---|---|---|---|
| 2018/0279947 A1 | 10/2018 | Ummat |
| 2018/0310892 A1 | 11/2018 | Perschbacher et al. |
| 2018/0325407 A1 | 11/2018 | Varadan et al. |
| 2019/0374103 A1 | 12/2019 | Hresko et al. |
| 2020/0046241 A1 | 2/2020 | Lam et al. |

OTHER PUBLICATIONS

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

Lifecor LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Pagan-Carlo, et al., "Encircling Overlapping Multipulse Shock Waveforms for Transthoracic Defibrillation," JACC Journals, Dec. 1998, vol. 32 Issue 7, p. 2065-2071.

The LifeVest Network/Patient Data Management System, Zoll, 2015, 2000503 Rev A.

WCD Performance for Clinical Review, Sullivan et al., "A Novel Wearable Cardioverter Defibrillator With Reduced False Alarm Rate," AHA 2017, University of Washington, Seattle, Washington.

* cited by examiner

SAMPLE COMPONENTS OF WEARABLE CARDIOVERTER DEFIBRILLATOR (WCD) SYSTEM

SAMPLE COMPONENTS OF EXTERNAL DEFIBRILLATOR

COMPONENTS OF SAMPLE WCD SYSTEM

*Event Marker Data Transfer Components*

WEARABLE CARDIOVERTER DEFIBRILLATOR (WCD) SYSTEM LOGGING EVENTS AND BROADCASTING STATE CHANGES AND SYSTEM STATUS INFORMATION TO EXTERNAL CLIENTS

CROSS REFERENCE TO RELATED PATENT APPLICATIONS

The present application is a continuation of U.S. application Ser. No. 16/396,415 filed Apr. 26, 2019 (pending) which claims the benefit of U.S. Application No. 62/662,892 filed Apr. 26, 2018. Said application Ser. No. 16/396,415, said Application No. 62/662,892, and Pub. No. US 2019/0329055 A1 are hereby incorporated herein by reference in their entireties for all purposes.

FIELD

The present disclosure generally relates to the field of medical devices. More particularly, an embodiment relates to a Wearable Cardioverter Defibrillator (WCD) system that is capable of logging events and/or broadcasting state changes and/or system status information to external clients.

BACKGROUND

When people suffer from some types of heart arrhythmias, the result may be that blood flow to various parts of the body is reduced. Some arrhythmias may even result in a Sudden Cardiac Arrest (SCA). SCA can lead to death very quickly, e.g., within 10 minutes unless treated in the interim. Some observers consider SCA to be the same as a heart attack, but it is not.

Some people have an increased risk of SCA. Such people include patients who have had a heart attack, or a prior SCA episode. A frequent recommendation for these people is to receive an Implantable Cardioverter Defibrillator (ICD). ICD is surgically implanted in the chest, and continuously monitors the patient's electrocardiogram (ECG). If certain types of heart arrhythmias are detected, then the ICD delivers an electric shock through the heart to avoid or reduce further complications.

As a further precaution, people who have been identified to have an increased risk of an SCA are sometimes given a Wearable Cardioverter Defibrillator (WCD) system, to wear until the time that their ICD is implanted. Early versions of such systems were called wearable cardiac defibrillator systems. A WCD system includes a harness, vest, belt, or other garment that the patient is to wear. The WCD system further includes electronic components, such as a defibrillator and electrodes, coupled to the harness, vest, or other garment. When the patient wears the WCD system, the electrodes may make good electrical contact with the patient's skin, and therefore can help sense the patient's ECG. If a shockable heart arrhythmia is detected from the ECG, then the defibrillator delivers an appropriate electric shock through the patient's body, and thus through the heart. This may restart the patient's heart and thus save that patient's life.

All subject matter discussed in this Background section of this document is not necessarily prior art, and may not be presumed to be prior art simply because it is presented in this Background section. Plus, any reference to any prior art in this description is not, and should not be taken as, an acknowledgement or any form of suggestion that such prior art forms parts of the common general knowledge in any art in any country. Along these lines, any recognition of problems in the prior art discussed in this Background section or associated with such subject matter should not be treated as prior art unless expressly stated to be prior art. Rather, the discussion of any subject matter in this Background section should be treated as part of the approach taken towards the particular problem by the inventor(s). This approach in and of itself may also be inventive.

BRIEF SUMMARY

The present description provides instances of Wearable Cardioverter Defibrillator (WCD) systems, devices, storage media that may store programs (or instructions), and methods, the use of which may help overcome problems and limitations of the prior art.

In an embodiment, a WCD system stores time-stamped data related to system "Event Markers" during run time, e.g., documenting the occurrence of a broad variety of events. The event data can be saved to a local storage device (e.g., in a database format). The local storage device may include a volatile memory device (e.g., for buffering), a non-volatile memory device (such as a removable SD (Secure Digital) card), or combinations thereof, so the events can be used for diagnostic and analytical purposes. Alternatively, the captured data corresponding to the Event Markers may be communicated via a wired connection (e.g., via a Universal Serial Bus (USB) cable, Ethernet cable, etc.) or wireless connection (e.g., via WiFi (Wireless Fidelity) communication, cellular communication, Bluetooth™ communication, etc.) to a separate computing device, the Internet, the cloud, etc.

This allows users to quickly determine the state of the system at any given time, and provide feedback to service/rescue personnel, clinicians, and physicians during patient use or patient consultation session. In one or more embodiments, the information transmitted and stored may include patient rhythms, patient activity, patient wear statistics as well as the current running state and activity of the system including state changes, alert button activity, and overall device status as will be further discussed herein.

These and other features and advantages of the claimed invention will become more readily apparent in view of the embodiments described and illustrated in this specification, namely in this written specification and the associated drawings.

DETAILED DESCRIPTION

Figure 1:
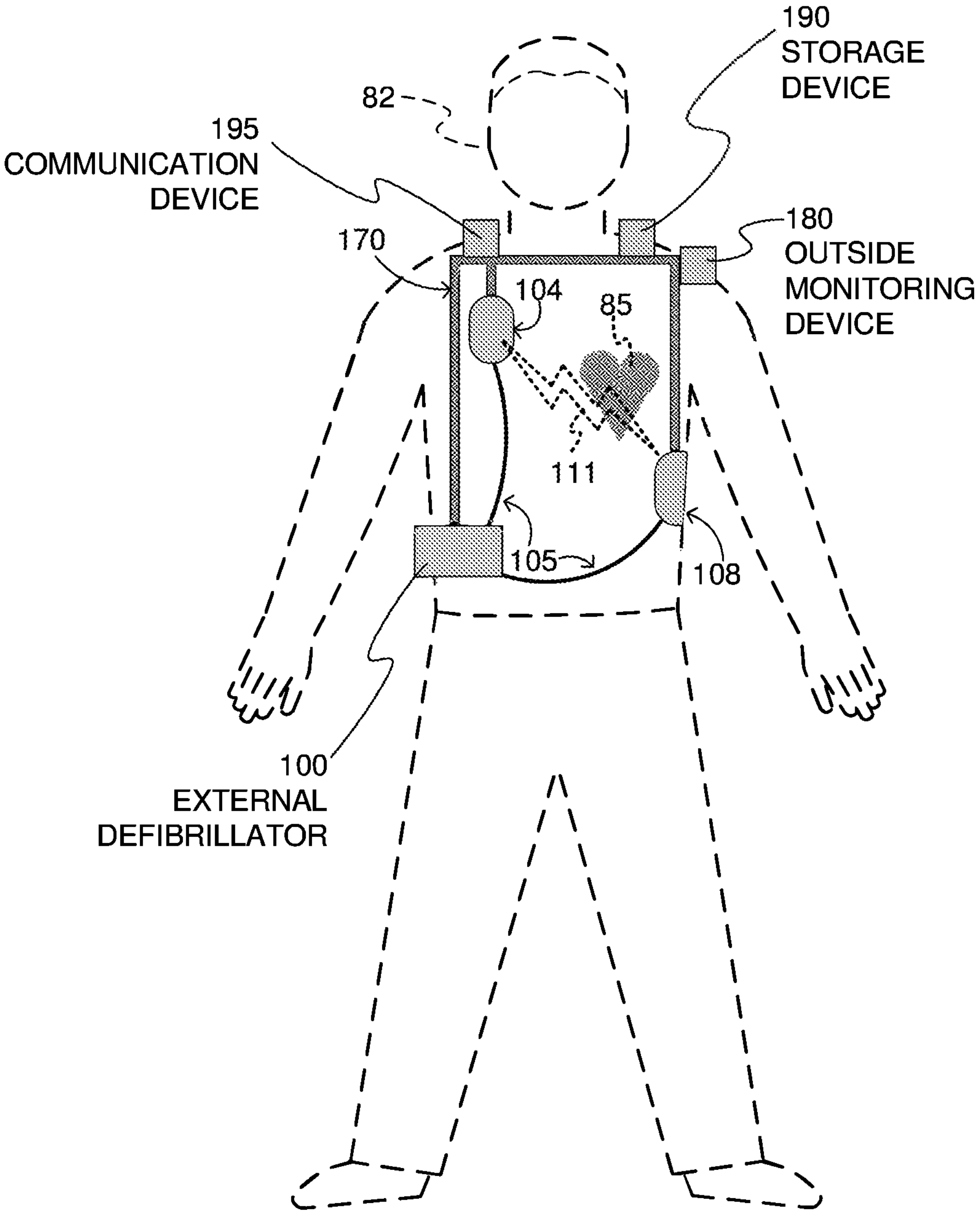
FIG. 1 is a diagram of components of a sample Wearable Cardioverter Defibrillator (WCD) system, made according to some embodiments.

In the following description, numerous specific details are set forth in order to provide a thorough understanding of various embodiments. However, various embodiments may be practiced without the specific details. In other instances, well-known methods, procedures, components, and circuits have not been described in detail so as not to obscure the particular embodiments. Further, various aspects of embodiments may be performed using various means, such as integrated semiconductor circuits ("hardware"), computer-readable instructions organized into one or more programs ("software"), or some combination of hardware and software. For the purposes of this disclosure reference to "logic" shall mean either hardware (such as logic circuitry or more generally circuitry or circuit), software, firmware, or some combination thereof.

Generally, in a closed system (e.g., without a large display), the device is not capable of providing detailed status information to users. Devices with limited storage and/or limited connectivity are not able to share detailed information with remote caregivers. To this end, some embodiments provide users (such as patients, physicians, clinicians, or engineering team members) insight regarding detailed information related to the state of the system during run-time or later during a patient evaluation or customer support session.

As mentioned above, the present description generally relates to Wearable Cardioverter Defibrillator (WCD) systems, devices, storage media that may store programs or instructions, and methods. Embodiments are now described in more detail. In one or more embodiments, a WCD system includes a support structure for wearing by an ambulatory patient. When worn, the support structure maintains electrodes on the patient's body (e.g., in electrical contact with the patient's body) to detect various conditions/signals as further discussed herein.

While some embodiments discussed herein may indicate that the patient is ambulatory, this is not a requirement for all embodiments. Hence, in one or more embodiments, the patient may be stationary or otherwise incapable of moving/walking around.

In an embodiment, a WCD system stores time-stamped data related to system "Event Markers" during run time, e.g., documenting the occurrence of a broad variety of events. The event data can be saved to a local storage device (e.g., in a database format). The local storage device may include a volatile memory device (e.g., for buffering), a non-volatile memory device (such as a removable SD (Secure Digital) card), or combinations thereof, so the events can be used for diagnostic and analytical purposes. Alternatively, the captured data corresponding to the Event Markers may be communicated via a wired connection (e.g., via a Universal Serial Bus (USB) cable, Ethernet cable, etc.) or wireless connection (e.g., via WiFi communication, cellular communication, Bluetooth™ communication, etc.) to a separate computing device, the Internet, the cloud, etc.

In some embodiments, the data corresponding to the event markers can be stored continuously or periodically during normal operation/run-time (e.g., on an SD card and/or communicated via wired or wireless connections to other storage devices) so that they can be viewed via an external/remote device (such as a desktop computer, a laptop, a tablet, a smartphone, etc.) for device analysis or diagnostic purposes.

In addition, the events may be uploaded to the cloud or the Internet, for example via an assistive mobile device such as a tablet with an application (or app), a mobile phone, a custom device, an integrated communication device, etc. Various wireless communication protocols may be used to communicate the event data between the WCD system component(s) and another device (such as the mobile phone, tablet, etc.) including, for example, WiFi (in accordance with IEEE 802.11x protocols including 802.11b, 802.11g, 802.11ac, 802.11ax, etc.), Bluetooth™, cellular communication protocols, etc. Such uploading may allow users to view patient and/or device-related information.

Further, the event data may be uploaded by request, automatically (e.g., periodically such as every two hours and the like), or in an emergency. During an emergency, the event data can be uploaded immediately, which would allow for timely analysis of issues or problems while the patient is still wearing the device.

In an embodiment, customer support can assist with diagnostics in the field since the information that is stored/transmitted would provide the current state of the system as well as the settings for various parameters during run-time. This allows engineering and support teams to trace the events back to the root cause of an issue.

In addition, as more information is learned about systems in the field, different cloud-base analytics can be developed using other information associated with the event markers to detect specific patient or device conditions. In an embodiment, AI (Artificial Intelligence) may be applied to at least a portion of the store and/or transmitted event marker data to determine failure causes/sources, solutions, etc.

A WCD system according to some embodiments may protect a patient by electrically restarting their heart if needed. Such a WCD system may have a number of components. These components can be provided separately as modules that can be interconnected, or can be combined with other components, and so on.

FIG. 1 depicts a patient 82. Patient 82 may also be referred to as a person and/or wearer, since the patient is wearing components of the WCD system. Patient 82 is ambulatory, which means that, while wearing the wearable portion of the WCD system, patient 82 can walk/move around and is not necessarily bed-ridden. While patient 82 may be considered to be also a "user" of the WCD system, this is not a requirement. For instance, a user of the wearable cardioverter defibrillator (WCD) may also be a clinician such as a doctor, nurse, emergency medical technician (EMT) or other similarly tasked individual or group of individuals. In some cases, a user may even be a bystander. The particular context of these and other related terms within this description should be interpreted accordingly.

A WCD system according to some embodiments can be configured to defibrillate the patient who is wearing the designated parts of the WCD system. Defibrillating can be by the WCD system delivering an electrical charge to the patient's body in the form of an electric shock. The electric shock can be delivered in one or more pulses.

In particular, FIG. 1 also depicts components of a WCD system made according to some embodiments. One such component is a support structure 170 that is wearable by ambulatory patient 82. Accordingly, support structure 170 is configured to be worn by ambulatory patient 82 for at least several hours per day, and for at least several days, even a few months. It will be understood that support structure 170 is shown only generically in FIG. 1, and in fact partly conceptually. FIG. 1 is provided merely to illustrate concepts about support structure 170, and is not to be construed as limiting how support structure 170 is implemented, or how it is worn.

Support structure 170 can be implemented in many different ways. For example, it can be implemented in a single component or a combination of multiple components. In some embodiments, support structure 170 could include a vest, a half-vest, a garment, etc. In such embodiments such items can be worn similarly to analogous articles of clothing. In some embodiments, support structure 170 could include a harness, one or more belts or straps, etc. In such embodiments, such items can be worn by the patient around the torso, hips, over the shoulder, etc. In some embodiments, support structure 170 can include a container or housing, which can even be waterproof. In such embodiments, the support structure can be worn by being attached to the patient's body by adhesive material, for example as shown and described in U.S. Pat. No. 8,024,037. Support structure 170 can even be implemented as described for the support structure of US Pat. App. No. US2017/0056682, which is incorporated herein by reference. Of course, in such embodiments, the person skilled in the art will recognize that additional components of the WCD system can be in the housing of a support structure instead of being attached externally to the support structure, for example as described in the US2017/0056682 document. There can be other examples.

FIG. 1 shows a sample external defibrillator 100. As described in more detail later in this document, some aspects of external defibrillator 100 include a housing and an energy storage module within the housing. As such, in the context of a WCD system, defibrillator 100 is sometimes called a main electronics module. The energy storage module can be configured to store an electrical charge. Other components can cause at least some of the stored electrical charge to be discharged via electrodes through the patient, so as to deliver one or more defibrillation shocks through the patient.

FIG. 1 also shows sample defibrillation electrodes 104, 108, which are coupled to external defibrillator 100 via electrode leads 105. Defibrillation electrodes 104, 108 can be configured to be worn by patient 82 in a number of ways. For instance, defibrillator 100 and defibrillation electrodes 104, 108 can be coupled to support structure 170, directly or indirectly. In other words, support structure 170 can be configured to be worn by ambulatory patient 82 so as to maintain at least one of electrodes 104, 108 on the body of ambulatory patient 82, while patient 82 is moving around, etc. The electrode can be thus maintained on the body by being attached to the skin of patient 82, simply pressed against the skin directly or through garments, etc. In some embodiments the electrode is not necessarily pressed against the skin, but becomes biased that way upon sensing a condition that could merit intervention by the WCD system. In addition, many of the components of defibrillator 100 can be considered coupled to support structure 170 directly, or indirectly via at least one of defibrillation electrodes 104, 108.

When defibrillation electrodes 104, 108 make good/sufficient electrical contact with the body of patient 82, defibrillator 100 can administer, via electrodes 104, 108, a brief, strong electric pulse 111 through the body. Pulse 111 is also known as shock, defibrillation shock, therapy, electrotherapy, therapy shock, etc. Pulse 111 is intended to go through and restart heart 85, in an effort to save the life of the patient 82. Pulse 111 can further include one or more pacing pulses (of lesser magnitude than the initial shock/pulse to restart the heart), e.g., to simply pace heart 85 if needed, and so on.

Some defibrillator implementations may decide whether to defibrillate or not based on an ECG signal of the patient. However, external defibrillator 100 may initiate defibrillation, or hold-off defibrillation, based on a variety of inputs, with the ECG signal merely being one of these inputs.

A WCD system according to some embodiments can obtain data from patient 82. For collecting such data, the WCD system may optionally include at least an outside monitoring device 180. Device 180 is called an "outside" device because it could be provided as a standalone device, for example not within the housing of the defibrillator 100. Alternatively, device 180 may be imported within the defibrillator 100 or as a single component. Device 180 can be configured to sense or monitor at least one local parameter. A local parameter can be a parameter of patient 82, or a parameter of the WCD system, or a parameter of the environment, as will be described later in this document.

For some of these parameters, device 180 may include one or more sensors or transducers. Each one of such sensors can be configured to sense a parameter of patient 82, and to render an input responsive to the sensed parameter. In some embodiments the input is quantitative, such as values of a sensed parameter; in other embodiments the input is qualitative, such as informing whether or not a threshold is crossed, and so on. Sometimes these inputs about patient 82 are also called physiological inputs and patient inputs. In some embodiments, a sensor can be construed more broadly, as encompassing many individual sensors.

Optionally, device 180 is physically coupled to support structure 170. In addition, device 180 may be communicatively coupled with other components that are coupled to support structure 170 such as a storage device 190 and/or a communication device 195. One or both of the devices 190/195 may be incorporated in the outside monitoring device 180 and/or the external defibrillator 100, or otherwise communicatively coupled to the outside monitoring device 180 and/or the external defibrillator 100 to facilitate storage/communication of the data collected regarding the parameter(s) and/or input(s) discussed herein. In an embodiment, the storage device 190 may include a processor (e.g., having one or more processor cores) to cause/manage storage of data in non-volatile and/or volatile memory (including non-volatile/volatile memory incorporated in the storage device 190 or elsewhere).

In some embodiments, one or more of the components of the WCD system may be customized for patient 82. This customization may include a number of aspects. For instance, support structure 170 can be fitted to the body of patient 82. For another instance, baseline physiological parameters of patient 82 can be measured, such as the heart rate of patient 82 while resting, while walking, motion detector outputs while walking, etc. The measured values of such baseline physiological parameters can be used to customize the WCD system, in order to make its diagnoses more accurate and/or quickly, since patients' bodies differ from one another. Of course, such parameter values can be stored in a memory of the WCD system (e.g., incorporated in the storage device 190 and/or in another component of system 82), and so on. Moreover, a programming interface can be made according to some embodiments, which receives such measured values of baseline physiological parameters. Such a programming interface may input automatically in the WCD system these, along with other data.

In an embodiment, the WCD system stores time-stamped data related to system "Event Markers" during run time, e.g., documenting the occurrence of a broad variety of events in the device/module 190. The event data can be saved to a local storage device such as device 190 (e.g., in a database format). The local storage device may include a volatile memory device (e.g., for buffering), a non-volatile memory device (such as a removable SD (Secure Digital) card), or combinations thereof, so the events can be used for diagnostic and analytical purposes. Alternatively, the captured data corresponding to the Event Markers may be communicated via a wired connection (e.g., via a Universal Serial Bus (USB) cable, Ethernet cable, etc.) or wireless connection (e.g., via WiFi communication, cellular communication, Bluetooth™ communication, etc.) provided by the communication device 195 to a separate computing device, the Internet, the cloud, etc.

In some embodiments, the data corresponding to the event markers can be stored continuously or periodically during normal operation/run-time (e.g., on an SD card and/or communicated via wired or wireless connections to other storage devices) so that they can be viewed via an external/remote device (such as a desktop computer, a laptop, a tablet, a smartphone, etc.) for device analysis or diagnostic purposes.

In addition, the events may be uploaded to the cloud or the Internet via the communication device 195, for example via an assistive mobile device such as a tablet with an application (or app), a mobile phone, a custom device, an integrated communication device, etc. Various wireless communication protocols may be used to communicate the event data between the WCD system component(s) and another device (such as the mobile phone, tablet, etc.) including, for example, WiFi (in accordance with IEEE 802.11x protocols including 802.11b, 802.11g, 802.11ac, 802.11ax, etc.), Bluetooth™, cellular communication protocols, etc. Such uploading may allow users to view patient and/or device-related information.

Figure 2:
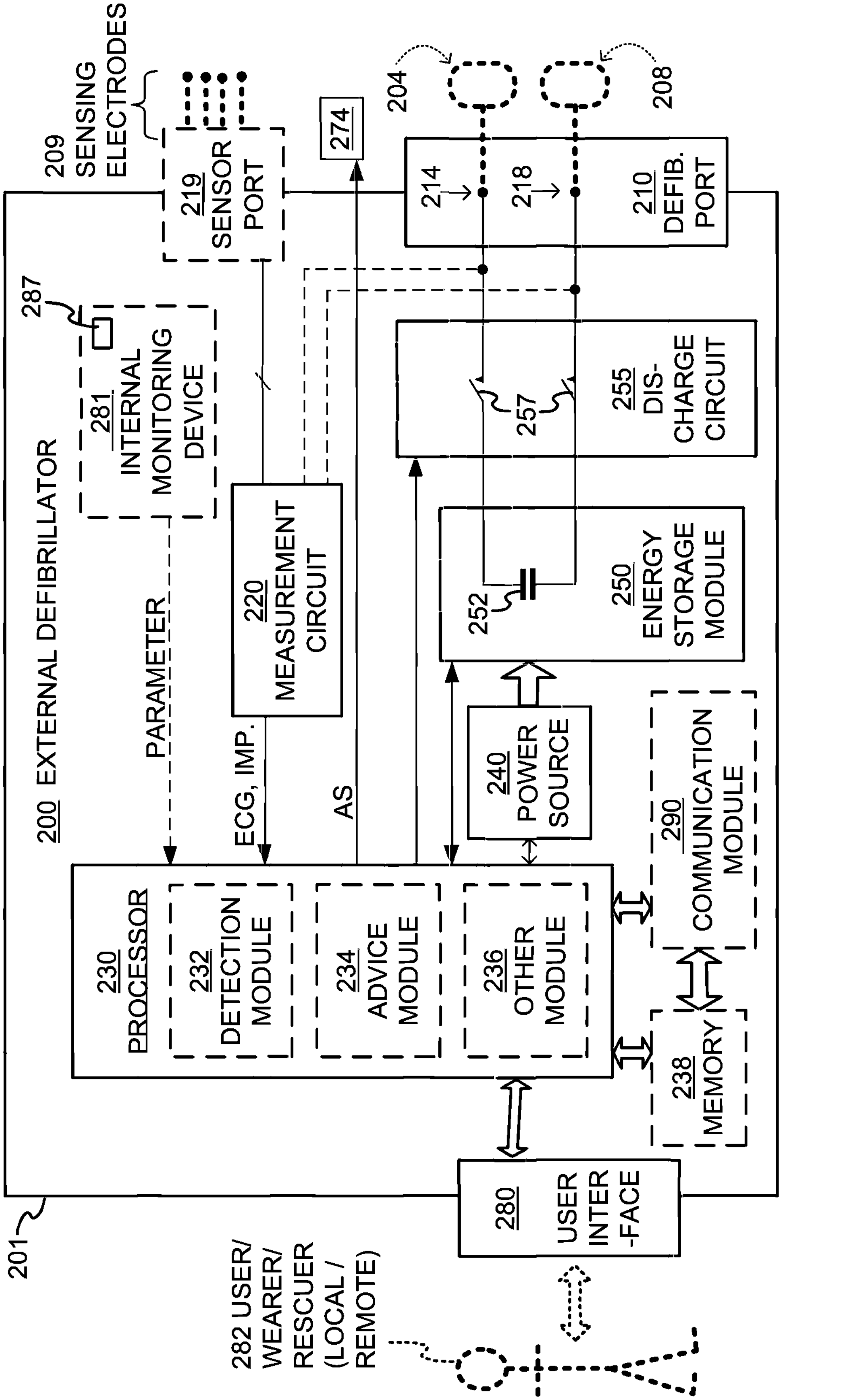
FIG. 2 is a diagram showing sample components of an external defibrillator, such as the one belonging in the system of FIG. 1, and which is made according to some embodiments.

FIG. 2 is a diagram showing components of an external defibrillator 200, made according to some embodiments. One or more of these components can be, for example, included in external defibrillator 100 of FIG. 1. The components shown in FIG. 2 can be provided in a housing 201, which may also be referred to as casing 201.

External defibrillator 200 is intended for a patient who would be wearing it, such as (e.g., ambulatory) patient 82 of FIG. 1. Defibrillator 200 may further include a user interface 280 for utilization by a user 282. User 282 may be patient 82, also known as wearer 82. Or, user 282 may be a local rescuer at the scene, such as a bystander who might offer assistance, or a trained person. Or, user 282 might be a remotely located trained caregiver in communication with the WCD system.

User interface 280 can be made in a number of ways. User interface 280 may include output devices, which can be visual, audible or tactile, for communicating to a user by outputting images, sounds or vibrations. Images, sounds, vibrations, and anything that can be perceived by user 282 can also be called human-perceptible indications (HPIs). There are many examples of output devices. For example, an output device can be a light, or a screen to display what is sensed, detected and/or measured, and provide visual feedback to rescuer 282 for their resuscitation attempts, and so on. Another output device may be a speaker, which can be configured to issue voice prompts, beeps, (e.g., loud) alarm sounds and/or words to warn bystanders, etc.

User interface 280 may further include input devices for receiving inputs from users. Such input devices may include various controls, such as pushbuttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

Defibrillator 200 may include an internal monitoring device 281. Device 281 is called an "internal" device because it is incorporated within housing 201. Monitoring device 281 can sense or monitor patient parameters such as patient physiological parameters, system parameters and/or environmental parameters, all of which can be called patient data. In other words, internal monitoring device 281 can be complementary or an alternative to outside monitoring device 180 of FIG. 1. Allocating which of the parameters are to be monitored by which of monitoring devices 180, 281 can be done according to design considerations. Device 281 may include one or more sensors, as also described elsewhere in this document.

Patient parameters may include patient physiological parameters. Patient physiological parameters may include, for example and without limitation, those physiological parameters that can be of any help in detecting (by the WCD system) of whether or not the patient is in need of a shock or other intervention or assistance. Patient physiological parameters may also optionally include the patient's medical history, event history and so on. Examples of such parameters include the patient's ECG, blood oxygen level, blood flow, blood pressure, blood perfusion, pulsatile change in light transmission or reflection properties of perfused tissue, heart sounds, heart wall motion, breathing sounds, and/or pulse. Accordingly, monitoring devices 180, 281 may include one or more sensors configured to acquire patient physiological signals. Examples of such sensors or transducers include one or more electrodes to detect ECG data, a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an $SpO_2$ (or blood oxygen) sensor, and so on. In view of this disclosure, it will be appreciated that such sensors can help detect the patient's pulse, and can therefore also be called pulse detection sensors, pulse sensors, and pulse rate sensors interchangeably. In addition, a person skilled in the art may implement other ways of performing pulse detection.

In some embodiments, a "local parameter" generally refers to a trend that can be detected in a monitored physiological parameter of patient 282. A trend can be detected by comparing values of parameters at different times over short and/or long terms. Parameters whose detected trends can particularly help a cardiac rehabilitation program include: a) cardiac function (e.g., ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from $SpO_2$, $CO_2$, or other parameters such as those mentioned above; f) respiratory function, respiratory rate, etc.; g) motion, level of activity; and so on. Once a trend is detected, it can be stored and/or reported via a communication link, along perhaps with a warning if warranted. From the report, a physician monitoring the progress of patient 282 will know about a condition that is either not improving or deteriorating.

Patient state parameters include recorded aspects of patient 282, such as motion, posture, whether they have spoken recently plus maybe also what they said, and so on, plus optionally the history of these parameters. Or, one of these monitoring devices could include a location sensor such as a Global Positioning System (GPS) location sensor. Such a sensor can detect the location, plus a speed can be detected as a rate of change of location over time. Many motion detectors output a motion signal that is indicative of the motion of the detector, and thus of the patient's body. Patient state parameters can be very helpful in narrowing down the determination of whether SCA is indeed taking place.

A WCD system made according to some embodiments may thus include a motion detector. In some embodiments, a motion detector can be implemented within monitoring device 180 or monitoring device 281. Such a motion detector can be made in many ways as is known in the art, for example by using an accelerometer. In this example, a motion detector 287 is implemented within monitoring device 281. A motion detector of a WCD system according to some embodiments can be configured to detect a motion event. A motion event can be defined as is convenient, for example a change in motion from a baseline motion or rest, etc. In such cases, a sensed patient parameter is motion.

System parameters of a WCD system can include system identification, battery status, system date and time, reports of self-testing, records of data entered, records of episodes and intervention, and so on. In response to the detected motion event, the motion detector may render or generate, from the detected motion event or motion, a motion detection input that can be received by a subsequent device or functionality.

Environmental parameters can include ambient temperature and pressure. Moreover, a humidity sensor may provide information as to whether or not it is likely raining. Presumed patient location could also be considered an environmental parameter. The patient location could be presumed, if monitoring device 180 or 281 includes a GPS location sensor as per the above, and if it is presumed that the patient is wearing the WCD system.

Defibrillator 200 may include a defibrillation port 210, which can be a socket in housing 201. Defibrillation port 210 includes electrical nodes 214, 218. Leads of defibrillation electrodes 204, 208, such as leads 105 of FIG. 1, can be plugged into defibrillation port 210, so as to make electrical contact with nodes 214, 218, respectively. It is also possible that defibrillation electrodes 204, 208 are coupled continuously to defibrillation port 210, instead. Either way, defibrillation port 210 can be used for guiding, via electrodes, to the wearer at least some of the electrical charge that has been stored in an energy storage module 250 that is described more fully later in this document. The electric charge can be used for the shock for defibrillation, pacing, and so on.

Defibrillator 200 may optionally also have a sensor port 219 in housing 201, which is also sometimes known as an ECG port. Sensor port 219 can be adapted for plugging in one or more sensing electrode(s) 209, which are also known as ECG electrodes and ECG leads. It is also possible that sensing electrodes 209 can be coupled continuously to sensor port 219, instead. Sensing electrodes 209 may include any type of transducers that can help sense an ECG signal, e.g., a 12-lead signal, or a signal from a different number of leads, especially if they make good/sufficient electrical contact with the body of the patient and in particular with the skin of the patient. As with defibrillation electrodes 204, 208, the support structure can be configured to be worn by patient 282 so as to maintain sensing electrodes 209 on a body of patient 282. For example, sensing electrodes 209 can be attached to the inside of support structure 170 for making good/sufficient electrical contact with the patient, similarly with defibrillation electrodes 204, 208.

Optionally a WCD system according to some embodiments also includes a fluid that it can deploy automatically between the electrodes and the patient's skin. The fluid can be conductive, such as by including an electrolyte, for establishing a better electrical contact between the electrodes and the skin. Electrically speaking, when the fluid is deployed, the electrical impedance between each electrode and the skin is reduced. Mechanically speaking, the fluid may be in the form of a low-viscosity gel, so that it does not flow away, after being dispensed, from the location it is released near the electrode. The fluid can be used for both defibrillation electrodes 204, 208, and for sensing electrodes 209.

The fluid may be initially stored in a fluid reservoir, not shown in FIG. 2. Such a fluid reservoir can be coupled to the support structure. In addition, a WCD system according to some embodiments further includes a fluid deploying mechanism 274. Fluid deploying mechanism 274 can be configured to cause at least some of the fluid to be released from the reservoir, and be deployed near one or both of the patient locations to which electrodes 204, 208 are configured to be attached to the patient. In some embodiments, fluid deploying mechanism 274 is activated prior to the electrical discharge responsive to receiving activation signal AS from a processor 230, which is described more fully later in this document.

In some embodiments, defibrillator 200 also includes a measurement circuit 220, as one or more of its working together with its sensors or transducers. Measurement circuit 220 senses one or more electrical physiological signals of the patient from sensor port 219, if provided. Even if defibrillator 200 lacks sensor port 219, measurement circuit 220 may optionally obtain physiological signals through nodes 214, 218 instead, when defibrillation electrodes 204, 208 are attached to the patient. In these cases, the input reflects an ECG measurement. The patient parameter can be an ECG, which can be sensed as a voltage difference between electrodes 204, 208. In addition, the patient parameter can be an impedance, which can be sensed between electrodes 204, 208 and/or between the connections of sensor port 219 considered pairwise. Sensing the impedance can be useful for detecting, among other things, whether these electrodes 204, 208 and/or sensing electrodes 209 are not making good/sufficient electrical contact with the patient's body. These patient physiological signals may be sensed when available. Measurement circuit 220 can then render or generate information about them as inputs, data, other signals, etc. As such, measurement circuit 220 can be configured to render a patient input responsive to a patient parameter sensed by a sensor. In some embodiments, measurement circuit 220 can be configured to render a patient input, such as values of an ECG signal, responsive to the ECG signal sensed by sensing electrodes 209. Moreover, the information rendered by measurement circuit 220 is output from it, but this information can be called an input because it is received as an input by a subsequent device or functionality.

Defibrillator 200 also includes a processor 230. Processor 230 may be implemented in a number of ways. Such ways include, by way of example and not of limitation, digital and/or analog processors such as microprocessors and Digital Signal Processors (DSPs), controllers such as microcontrollers, software running in a machine, programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on. Further, the processor 230 can include one or more processor cores, one or more caches (such as level 1 (L1), level 2 (L2), level 3 (L3) caches, and so on).

Processor 230 may include, or have access to, a non-transitory computer-readable storage medium, such as memory 238 that is described more fully later in this document. Such a memory can have a non-volatile component for storage of machine-readable and machine-executable instructions. A set of such instructions can also be called a program. The instructions, which may also be referred to as "software," generally provide functionality by performing acts, operations and/or methods as may be disclosed herein or understood by one skilled in the art in view of the disclosed embodiments. In some embodiments, and as a matter of convention used herein, instances of the software may be referred to as a "module" and by other similar terms. Generally, a module includes a set of the instructions so as to offer or fulfill a particular functionality. Embodiments of modules and the functionality delivered are not limited by the embodiments described in this document. Also, "software" may include a software application, operating system, kernel, or firmware, as well as combinations thereof.

Processor 230 can be considered to have a number of modules. One such module can be a detection module 232. Detection module 232 can include a Ventricular Fibrillation (VF) detector. The patient's sensed ECG from measurement circuit 220, which can be available as inputs, data that reflect values, or values of other signals, may be used by the VF detector to determine whether the patient is experiencing VF. Detecting VF is useful, because VF results in SCA. Detection module 232 can also include a Ventricular Tachycardia (VT) detector, and so on. Also, detection module 232 may be implemented outside of the processor 230.

Another such module in (or coupled to) processor 230 can be an advice module 234, which generates advice for what to do. The advice can be based on outputs of detection module 232. There can be many types of advice according to some embodiments. In some embodiments, the advice is a shock/no shock determination that processor 230 can make, for example via advice module 234. The shock/no shock determination can be made by executing a stored Shock Advisory Algorithm. A Shock Advisory Algorithm can make a shock/no shock determination from one or more ECG signals that are captured according to some embodiments, and determine whether or not a shock criterion is met. The determination can be made from a rhythm analysis of the captured ECG signal or otherwise.

In some embodiments, when the determination is to shock, an electrical charge is delivered to the patient. Delivering the electrical charge is also known as discharging and shocking the patient. As mentioned above, such can be for defibrillation, pacing, and so on.

In perfect conditions, a very reliable shock/no shock determination can be made from a segment of the sensed ECG signal of the patient. In practice, however, the ECG signal is often corrupted by electrical noise, which makes it difficult to analyze. Too much noise sometimes causes an incorrect detection of a heart arrhythmia, resulting in a false alarm to the patient. Noisy ECG signals may be handled as described in U.S. patent application Ser. No. 16/037,990, filed on Jul. 17, 2018 and since published as US 20190030351 A1, and also in US patent application Ser. No. 16/038,007, filed on Jul. 17, 2018 and since published as US 20190030352 A1, both by the same applicant and incorporated herein by reference.

Processor 230 can include additional modules, such as other module 236, for other functions. In addition, if internal monitoring device 281 is indeed provided, processor 230 may receive its inputs, etc. Further, modules of the processor 230 may be provided elsewhere, as software, firmware, or combinations thereof.

Defibrillator 200 optionally further includes a memory 238, which can work together with processor 230. Memory 238 may be implemented in a number of ways. Such ways include, by way of example and not of limitation, volatile memories, Nonvolatile Memories (NVM), Read-Only Memories (ROM), Random Access Memories (RAM), magnetic disk storage media, optical storage media, smart cards, flash memory devices, any combination of these, and so on. Memory 238 is thus a non-transitory computer-readable storage medium. Memory 238, if provided, can include programs for processor 230, which processor 230 may be able to read and execute. More particularly, the programs can include sets of instructions in the form of code, which processor 230 may be able to execute upon reading. Executing is performed by physical manipulations of physical quantities, and may result in functions, operations, processes, acts, actions and/or methods to be performed, and/or the processor to cause other devices or components or blocks to perform such functions, operations, processes, acts, actions and/or methods. The programs can be operational for the needs of processor 230, and can also include protocols and ways that decisions can be made by detection module 232, advice module 234, and/or other module 236. In addition, memory 238 can store prompts for user 282, if this user is a local rescuer. Moreover, memory 238 can store data. This data can include patient data, system data, and/or environmental data, for example as learned/detected by internal monitoring device 281 and/or outside monitoring device 180. The data can be stored in memory 238 before it is transmitted out of defibrillator 200, or be stored there after it is received by defibrillator 200.

Defibrillator 200 can optionally include a communication module 290, for establishing one or more wired or wireless communication links with other devices of other entities, such as a remote assistance center, Emergency Medical Services (EMS), and so on. The communication links can be used to transfer data and commands. The data may be patient data, event information, therapy attempted, CPR performance, system data, environmental data, and so on. For example, communication module 290 may transmit wirelessly (e.g., on a periodic basis such as daily, hourly, etc.) heart rate, respiratory rate, and/or other vital signs data to a server accessible over the Internet, for instance as described in US 20140043149. This data can be analyzed directly by the patient's physician and can also be analyzed automatically by algorithms designed to detect a developing illness/condition and then notify medical personnel via text, email, phone, etc. Module 290 may also include one or more other components such as an antenna, portions of a processor, supporting electronics, outlet for a telephone or a network cable, etc.

Defibrillator 200 may also include a power source 240 (which may be outside or inside the casing 201). To enable portability of defibrillator 200, power source 240 may include a battery. Such a battery is implemented as a battery pack, which can be rechargeable or not. Sometimes a combination is used of rechargeable and non-rechargeable battery packs. Other embodiments of power source 240 can include an AC (Alternating Current) power override, for where AC power will be available, an energy-storing capacitor, and so on. Appropriate components may be included to provide for charging or replacing power source 240. In some embodiments, power source 240 is controlled and/or monitored by processor 230.

Defibrillator 200 may additionally include an energy storage module 250. Energy storage module 250 can be coupled to the support structure of the WCD system, for example either directly or via the electrodes and their leads. Module 250 is where some electrical energy can be stored temporarily in the form of an electrical charge, when preparing it for discharge to administer a shock. In some embodiments, module 250 can be charged from power source 240 to the desired amount of energy, e.g., as controlled by processor 230 or another controller (where the controller may be embedded with the power source 240 in an embodiment). In an implementation, module 250 includes a capacitor 252, which can be a single capacitor or a system of capacitors, and so on. In some embodiments, energy storage module 250 includes a device that exhibits high power density, such as an ultra-capacitor. As described above, capacitor 252 can store energy in the form of an electrical charge, e.g., for delivering a shock to the patient.

A decision to shock can be made responsive to the shock criterion being met, as per the above-mentioned determination. When the decision is to shock, processor 230 can be configured to cause at least some or all of the electrical charge stored in module 250 to be discharged through patient 82 while the support structure is worn by patient 82, so as to deliver a shock 111 to patient 82 of FIG. 1.

For causing the discharge, defibrillator 200 further includes a discharge circuit 255. When the decision is to shock, processor 230 can be configured to control discharge circuit 255 to discharge through the patient at least some of all of the electrical charge stored in energy storage module 250. Discharging can be to nodes 214, 218, and from there to defibrillation electrodes 204, 208, so as to cause a shock to be delivered to the patient. Circuit 255 can include one or more switches 257. Switches 257 can be made in a number of ways, such as by an H-bridge, a power transistor, and so on. Circuit 255 could also be thus controlled via processor 230, and/or user interface 280 or other logic.

A time waveform of the discharge may be controlled by thus controlling discharge circuit 255. The amount of energy of the discharge can be controlled by how much energy storage module has been charged, and also by how long discharge circuit 255 is controlled to remain open.

In one or more embodiments, storage device 190 of FIG. 1 includes memory 238. Also, communication device 195 may include the communication module 290.

Defibrillator 200 can optionally include other components.

Figure 3:
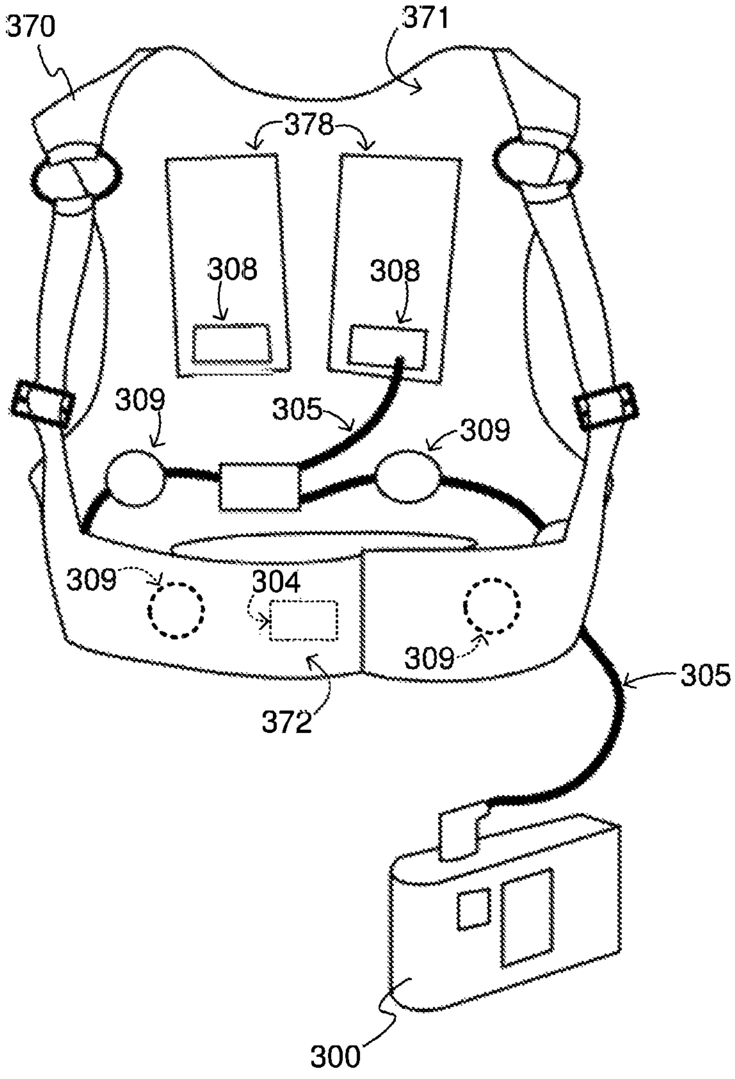
FIG. 3 is a diagram of sample embodiments of components of a WCD system.

FIG. 3 is a diagram of sample embodiments of components of an WCD system. A support structure 370 includes a vest-like wearable garment. Support structure 370 has a back side 371, and a front side 372 that closes in front of the chest of the patient.

The WCD system of FIG. 3 also includes an external defibrillator 300. FIG. 3 does not show any support for external defibrillator 300, which may be carried in a purse, on a belt, by a strap over the shoulder, and so on. Wires 305 connect external defibrillator 300 to electrodes 304, 308, 309. Of those, electrodes 304, 308 are defibrillation electrodes, and electrodes 309 are ECG sensing electrodes.

Support structure 370 is configured to be worn by the (e.g., ambulatory) patient so as to maintain electrodes 304, 308, 309 on a body of the patient. Indeed, back defibrillation electrodes 308 are maintained in pockets 378. The inside of pockets 378 can be made with loose netting, so that electrodes 308 can contact the back of the patient, especially with the help of the conductive fluid that has been deployed. In addition, sensing electrodes 309 are maintained in positions that surround the patient's torso, for sensing ECG signals and/or the impedance of the patient.

ECG signals in a WCD system may include too much electrical noise to be useful in some situations/environments. To ameliorate the problem, multiple ECG sensing electrodes 309 can be provided, for presenting many options to processor 230 of FIG. 2.

Figure 4:
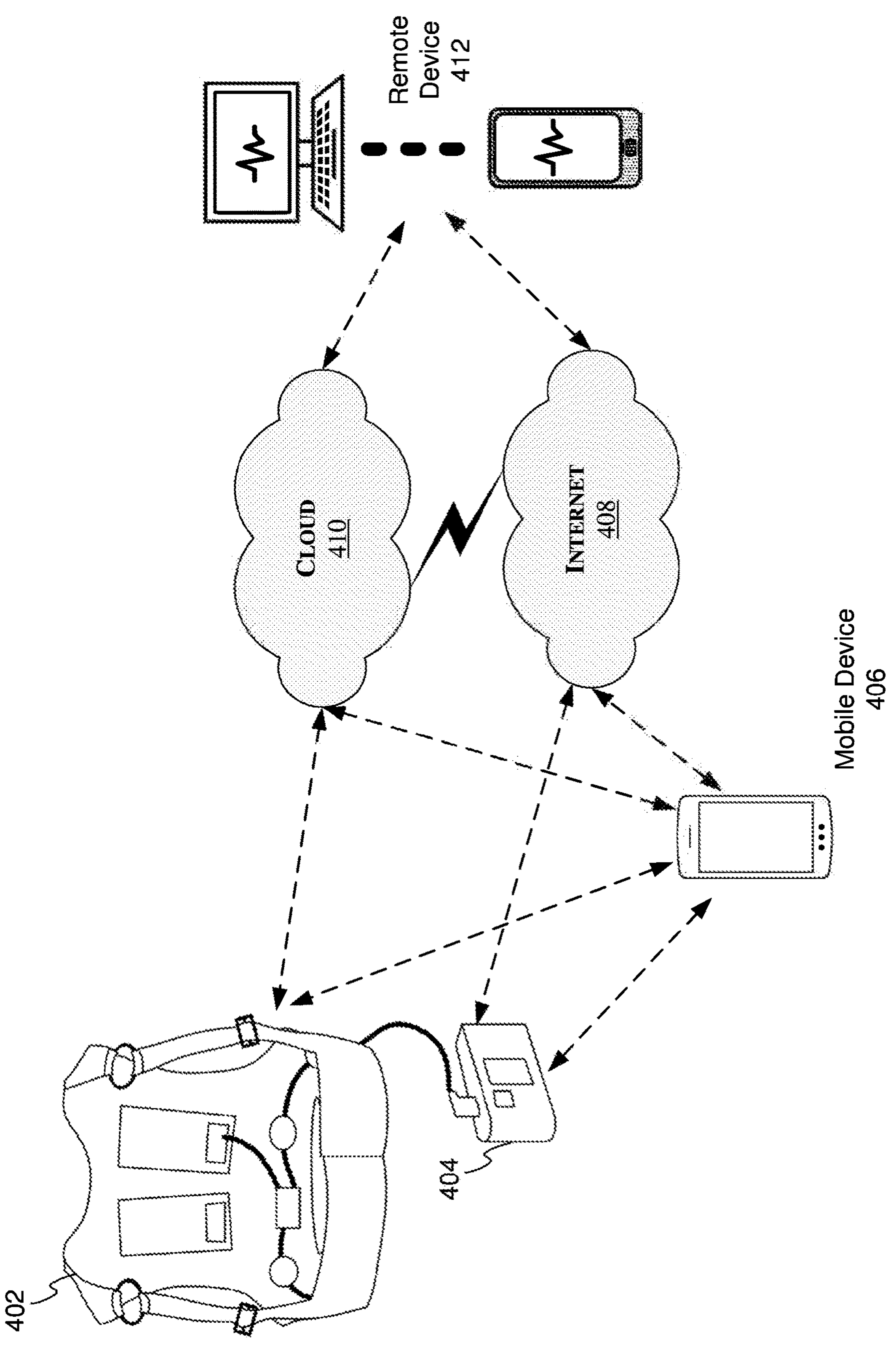
FIG. 4 illustrates a block diagram of components associated with flow of event marker data, according to an embodiment.

FIG. 4 illustrates a block diagram of components associated with flow of event marker data, according to an embodiment. As shown, a WCD system support structure 402 may include various components (see, e.g., the discussion with reference to previous figures) including a storage device to store event marker data. The storage device may be provided in a component attached directly to the support structure 402 (such as a hub) or in a device electrically coupled to the structure such as an external defibrillator 404.

The stored data is then transmitted either directly or via another device (such as a mobile device 406) to a network (such as the Internet 408, the cloud 410, etc.). The network can then make the stored data available to a remote device 412, which as previously mentioned may include any type of computing device, including a desktop computer, a laptop, a smartphone, a tablet, etc. for viewing by a user.

Figure 5:
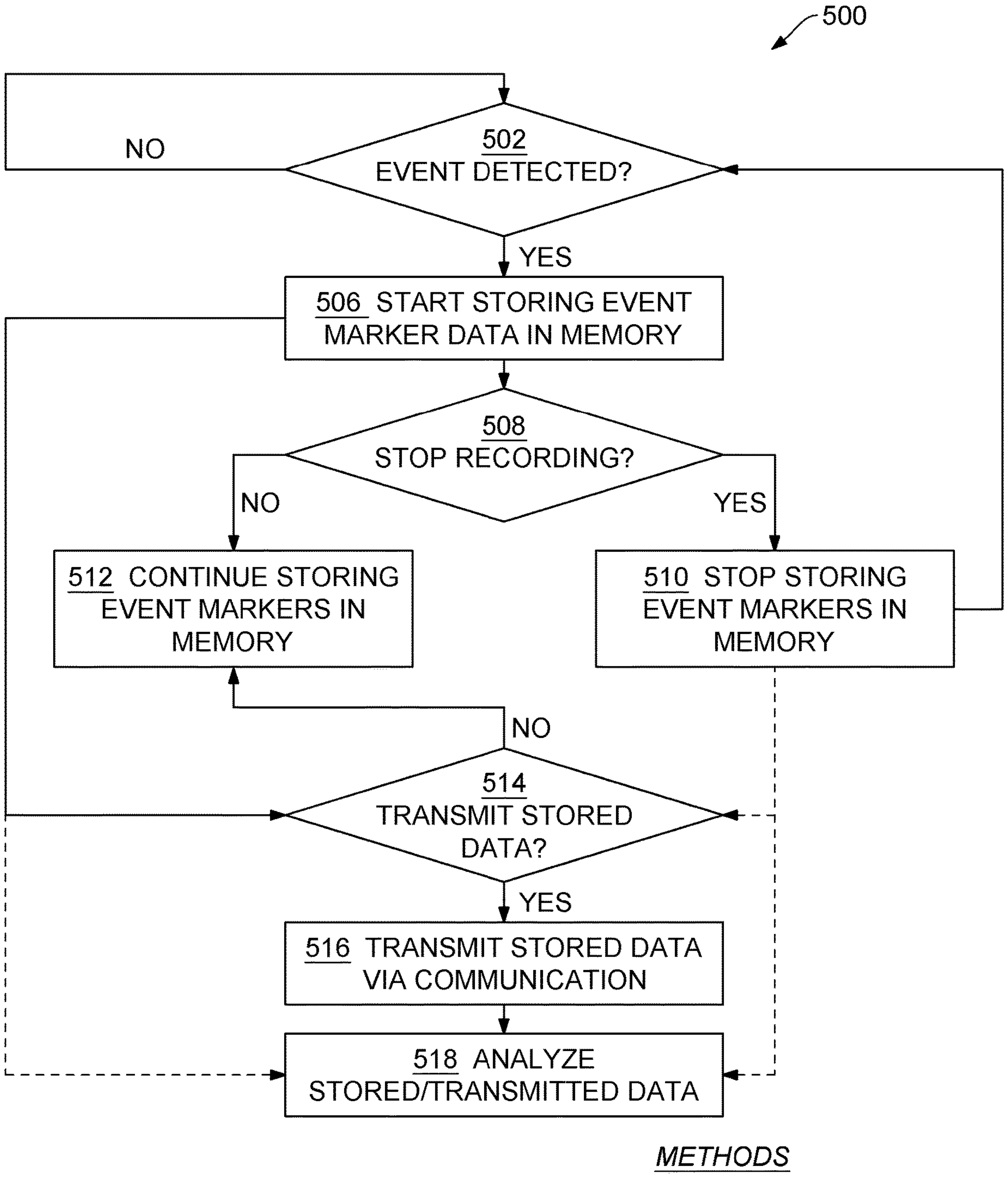
FIG. 5 illustrates a flow diagram of a method to log and transmit event marker data, according to an embodiment.

FIG. 5 illustrates a flow diagram of a method 500 to log and transmit event marker data, according to an embodiment. One or more operations of the method 500 may be performed by logic/components discussed herein with reference to other figures (including for example storage device 190, communication device 195, processor(s) (such as processor 230, a processor coupled/embedded with storage device 190, etc.).

In an embodiment, occurrence of the event at 502 is performed based at least in part on detection of one or more parameters by one or more sensors (e.g., GPS, accelerometer, temperature, etc. as further discussed below) or a signal generated by one or more of the sensing electrodes 209. Hence, the one or more sensors are to detect one or more parameters detected by a GPS sensor, an accelerometer sensor, a temperature sensor, etc.

Referring to FIGS. 1-5, upon detection of an event at 502, the WCD system (e.g., via a processor) starts storing time-stamped data related to system "Event Markers" in memory at 506 (e.g., during run time to document the occurrence of a broad variety of events). Storage of event marker data may be done by a processor (such as processor 230, a processor coupled/embedded with storage device 190, etc.). The event data can be saved to a local storage device such as device 190 (e.g., in a database format). The local storage device may include a volatile memory device (e.g., for buffering), a non-volatile memory device (such as a removable SD (Secure Digital) card), or combinations thereof.

At operation 508, it is determined whether to stop recording/storing the event marker data. The event marker data may be stored continuously, periodically, or for a select period of time after occurrence of the event. Hence, after the select period of time or expiration of a period (or even in response to a command from a user), operation 510 causes the storage of the event marker data to stop. Otherwise, the event marker storage is continued at operation 512, e.g., if period recording or select time period has not expired (or no command to stop has been received).

While data is being stored per operation 506/512, or if the storage of data is stopped at 510, operation 514 determines whether to transmit all or a portion of the stored data to a remote device (such as the Internet, the cloud, another computing device, etc.). If no transmission is required, then the method continues with operations 512 and/or 502 (e.g., after operation 510). Otherwise, operation 516 causes transmission of the stored data via a communication device (e.g., communication module 290, communication device 195, another computing device such as a smartphone, laptop, tablet, etc. that facilitates communication between the storage device 190 (or memory 238) and a remote device.

In this fashion, the data stored and/or transmitted can be analyzed at 518 to detect a patient condition or a WCD system/component condition. The analysis could be done locally by the processors provided or coupled to the WCD system, or a device in wired or wireless communication with components of the WCD system such as an app running on a smartphone, laptop, tablet, etc. Hence, the event data can be used for diagnostic and analytical purposes as discussed herein. Alternatively, the captured data corresponding to the Event Markers may be communicated via a wired connection (e.g., via a Universal Serial Bus (USB) cable, Ethernet cable, etc.) or wireless connection (e.g., via WiFi communication, cellular communication, Bluetooth™ communication, etc.) provided by the communication device 195 to a separate computing device, the Internet, the cloud, etc.

In some embodiments, the data corresponding to the event markers can be stored continuously or periodically (or even for a select/configurable period of time) during normal operation/run-time (e.g., on an SD card and/or communicated via wired or wireless connections to other storage devices), so that they can be viewed via an external/remote device (such as a desktop computer, a laptop, a tablet, a smartphone, etc.) for device analysis or diagnostic purposes.

In addition, the events may be uploaded to the cloud or the Internet at operation 416 via the communication device 195, for example via an assistive mobile device such as a tablet with an application (or app), a mobile phone, a custom device, an integrated communication device, etc. Various wireless communication protocols may be used to communicate the event data between the WCD system component(s) and another device (such as the mobile phone, tablet, etc.) including, for example, WiFi (in accordance with IEEE 802.11x protocols including 802.11b, 802.11g, 802.11ac, 802.11ax, etc.), Bluetooth™, cellular communication protocols, etc. Such uploading may allow users to view patient and/or device-related information.

Each event marker can come from a broad range of events the device encounters and contain detailed information about the event including the time the event occurred, an event ID (Identifier), and/or additional event-specific information. Some example categories of Event Markers are listed below; this is not an exhaustive list:

- Patient Information Management
- Programmable Parameter Operations
- Episode Operations
- Arrhythmia Detection and Normal Rhythm Detections
- Defibrillation Charging Operations
- Shock Delivery Operations
- Power On
- Battery Information
- ECG Electrode Contact Status
- Defibrillator Electrode Contact Status
- Self-Test/Service Needed/Service Required Conditions
- System Connectivity Changes
- User Interface Changes/Updates/Activity (e.g., Vibration and Audio)
- Alarm Issuing
- Alert Button Activity
- Software Update Status
- Processor Speed Scaling Changes
- Operational Mode Changes Different types of analysis/diagnostics could be performed with the stored Event Marker data. Examples include but are not limited to:

- Detect an intermittent problem with a specific ECG electrode if repeated Event
- Markers are present
- Detect patients who are receiving an excessive number of equipment alarms
- Track the health of the WCD's battery by looking at Battery Information over a period of time (e.g., days, weeks, etc.)
- Detect changes in Device Programming
- Detect potential security issues if repeated Connectivity attempts are made
- Determine a proper fit over time for a patient with continuous Excessive Noise events
- Detect when storage capacity is getting low and alert user or service center
- Detect wear time compliance with the option to send notification to the patient if it is not met
- Detect patient activity which could be used as a motivator to continue progress or encourage patients to meet a goal
- Software validation teams could use the UI events to determine that the system display is as expected at any point in time In one or more embodiments, the event marker data is analyzed to determine one or more conditions as follows:

- Use a combination of electrode behavior (not just one) to interpret if patient has a good/acceptable or poor fit. An ML (Machine Learning) or AI (Artificial Intelligence) algorithm could be used to predict good or poor fit based on learned data from similar patients (e.g., have about the same height, size, weight, etc.).
- Discriminate quality of ECG, and detect finer levels of noise being injected into the signal as a way of detecting dry skin in contact with electrodes. This could also potentially leverage ML/AI algorithms to predict condition.
- Pressure sensors could be fitted to the garment to enhance detection of objective fit quality. Event markers could be used to indicate when fit is degrading over time with wear. Since this typically correlates to wearing the garment, it could be used as a "wash" reminder to the user/wearer. Washing the garment would then return the garment to its standard state to address such degrading.
- Use respiration as a way of confirming quality of ECG signals—either to confirm leads-off is in synch with the respiration or if respiration could correlate with good or poor fit metric.
- Accelerometer data could be used to determine if it is a cause of the noise being injected into the system which would affect the fit of the garment.
  - ACCL (or accelerometer) could also be used to identify quiet time for system to measure "noise floor" for better assessing the fit or skin conditioning of the patient. As discussed herein, a "noise floor" generally refers to a signal corresponding to the sum of all noise sources and unwanted signals within a system, wherein noise is defined as any signal other than the signal being desirable/measured.

ACCL could also be used for detecting if the system is being abused or used inappropriately. An example would be if the ACCL is reading wild swings in X, Y, Z values when being violently swung around or knocked against something for an extended period of time.

Temperature sensors coupled to the WCD system could be used to detect (e.g., as in ACCL above) abuse or inappropriate use of the system.

Significant changes in temperature (for a monitor-based temp sensor) can be used as a way of detecting when the patient moves to different environments. Events marking this behavior could be analyzed for patterns using an ML/AI algorithm.

Detect when the device (monitor, or WCD component) is exposed to extreme temperatures.

Alarm or send emergency notification if healthy ECG is being observed in extreme temperatures.

Movement could also be correlated with WCD detected temperature sensor to track activity level (e.g., along with heart rate) to indicate significant exertion, or physical activity. Again, this could be indicated via an event marker.

In one or more embodiments, device diagnostics related to hardware or system failures include:

Assessing the range of the ambient light sensor over time to detect when the light tube may be degraded or failing. This could be implemented using a Machine Learning and/or Artificial Intelligence algorithm or straight deductive algorithm for checking the failure. For example, software/logic could calibrate the ambient light sensor against the light tube on initial use to determine the normal or expected behavior. Over time through various measurements and learned expected behavior through monitoring, the software/logic could detect abnormalities which could then be used to determine degradation over time. Those failures could be saved to the system Event Log (as an event marker) which would be used to notify a service depot of a potential hardware issue.

Similar and related diagnostic issues may include:

Battery communication problems.

Changes in capacitor charging times.

Testing if there is electrical continuity in the cable for the alert button.

Could also be implemented by testing the presence of a haptic drive motor.

Statistics could be gathered on any number of events stored to determine if there are trends or changes in the events that are gathered by a device. For example, for internal failures that are trending up—see battery failure example above. Frequency of non-critical self-test failures would potentially indicate a more serious problem may be about to occur.

The ML/AI/Data Mining algorithms could be used to define a "good working" device from known event patterns, and when a device falls outside of this pattern or state, then it would be flagged as a potential problem worthy of at least a follow up call to the patient—being more proactive than reactive.

Also, a GPS sensor could detect when the device is above a 30,000 foot elevation. Excessive duration of a device above this altitude is at risk of experiencing an Flash memory failure.

In some embodiments, the data is stored to an SD card to be retrieved after data is collected. In other embodiments, the data could be transferred to a smart device such as a phone, tablet, PC, smartwatch, etc. I assume then that the WCD would include additional circuits to connect with those devices such as Bluetooth™, Zigbee™, WiFi, etc. Then the smart device would in turn upload the data to the cloud via WiFi or a cellular connection. Once in the cloud the data can be retrieved by the manufacturer for diagnostics, or by the medical provider to analyze the medical data, perhaps even in real time. A cell transceiver could be included in the WCD to achieve the same data transfer path which would remove the need for a smart device.

Figure 6:
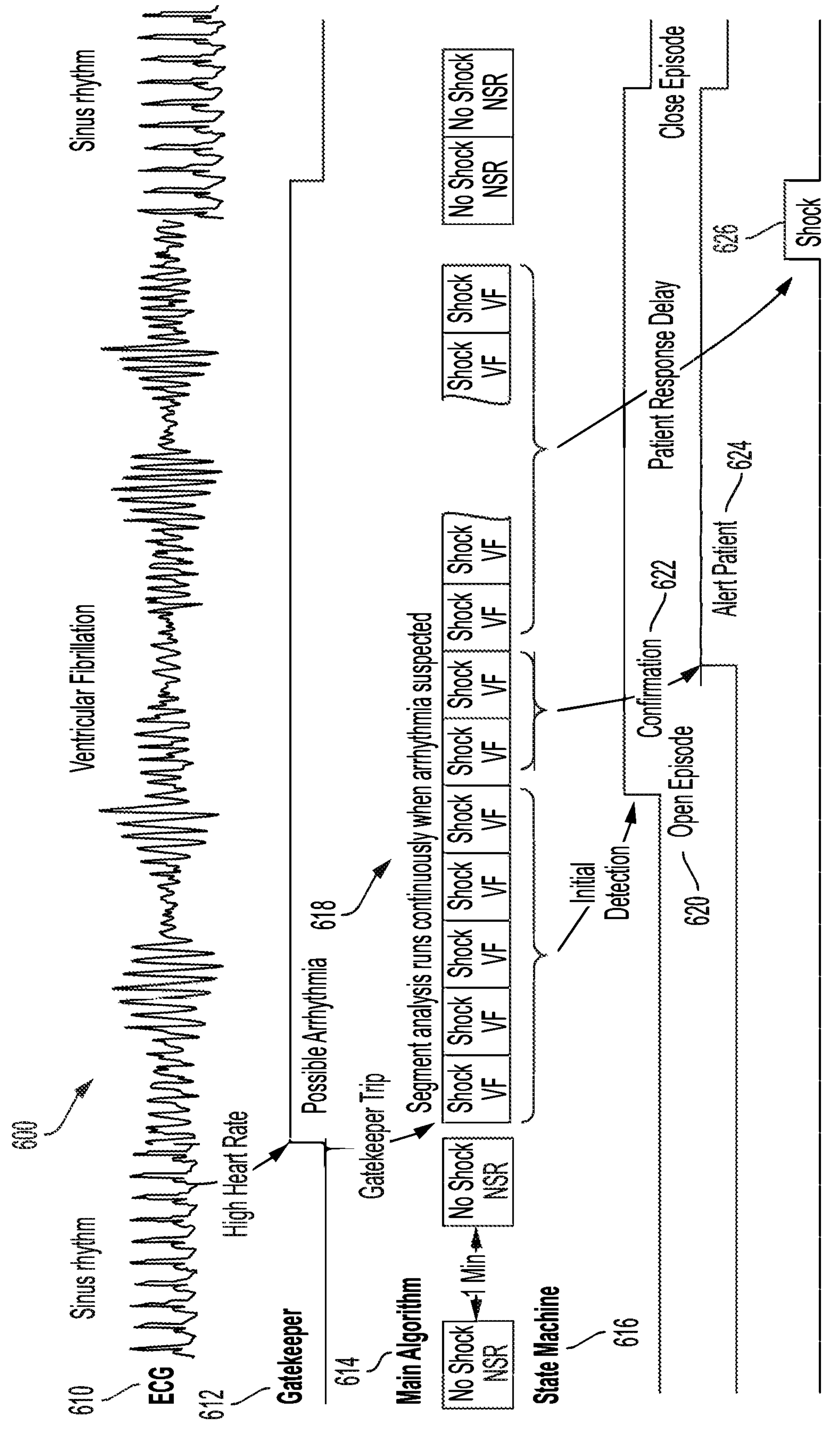
FIG. 6 is a diagram of segment based processing used in a WCD system in accordance with one or more embodiments.

Referring now to FIG. 6, a diagram of segment based processing used in a WCD system in accordance with one or more embodiments will be discussed. The segment-based processing analysis 600 shown in FIG. 6 is utilized by WCD system of FIG. 1 to make shock/no-shock decisions based at least in part on successive segments of ECG data. The segments can be 4.8 seconds in duration, although the scope of the disclosed subject matter is not limited in this respect.

The WCD system monitors and analyzes ECG data 610 to make a shock/no-shock decision. A gatekeeper function 612 may be used to provide an early indication that an arrhythmia may be present in the patient. An example embodiment of this gatekeeper functionality is disclosed in U.S. application Ser. No. 15/715,500 filed Sep. 26, 2017, published as US20180093102 A1 on Apr. 5, 2018, which is incorporated herein by reference in its entirety for all purposes. In some embodiments, if an arrhythmia is suspected with the gatekeeper function 612, then the main rhythm analysis algorithm 614 is triggered to start analyzing successive segments 618 of ECG data, and a shock/no-shock decision is made for each of the individual segments 618. If a string of the segments 618, for example six segments, provide a shock decision, then an episode is opened (Open Episode) 620 in a state machine 616. In some embodiments, this starts an internal storage of ECG information in a memory of the WCD system for later review. After the Open Episode 620, if the shockable rhythm persists for a confirmation period, for example for two or more segments for ventricular fibrillation (VF) or nineteen or more segments for ventricular tachycardia (VT) in some embodiments, then the patient alert sequence (Alert Patient) 624 is initiated. If the patient does not respond within a specified amount of time after initiation of the patient alert sequence, for example after 20 seconds, then a shock (Shock) 626 is delivered to the patient.

Figure 7:
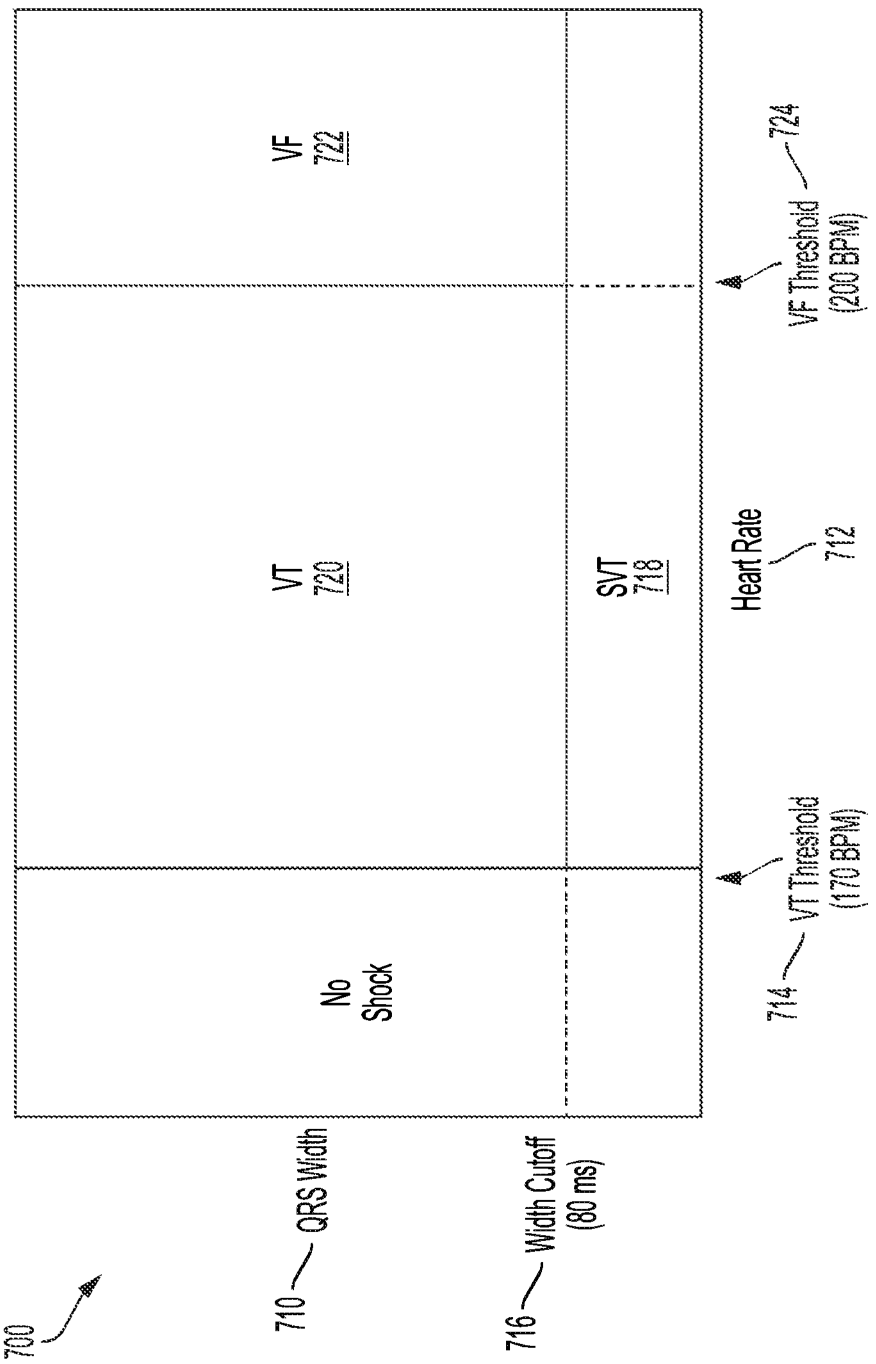
FIG. 7 is a diagram of a shock decision method used in a WCD system in accordance with one or more embodiments.

Referring now to FIG. 7, a diagram of a shock decision method used in a WCD system in accordance with one or more embodiments will be discussed. In one or more embodiments, the WCD system can utilize a rhythm analysis algorithm (RAA) to make shock/no-shock decisions based on the patient's heart rate and QRS width according to graph 700. QRS 710 width is shown on the vertical axis, and heart rate 712 is shown on the horizontal axis. As discussed herein, "QRS" complex generally refers to the combination of three of graphical deflections on an electrocardiogram, or the most visually prominent spike on an ECG line. As shown in FIG. 7, all rhythms with a heartrate below the ventricular tachycardia (VT) threshold 714, for example 170 beats per minute (BPM), are considered non-shockable. All rhythms below the QRS width cutoff 716, for example 80 milliseconds (ms), are considered non-shockable as well. Above the VT threshold 714, narrow rhythms are classified as super ventricular tachycardia (SVT) 718. Fast, wide rhythms are classified either as ventricular tachycardia (VT) 720 or ventricular fibrillation (VF) 722, depending on the heart rate.

For example, in some embodiments heart rate above a VF threshold 724 of 200 BPM with a QRS width above the QRS width cutoff threshold 716 would be classified as VF 722. Both VT 720 and VF 722 are considered shockable conditions.

Figure 8:
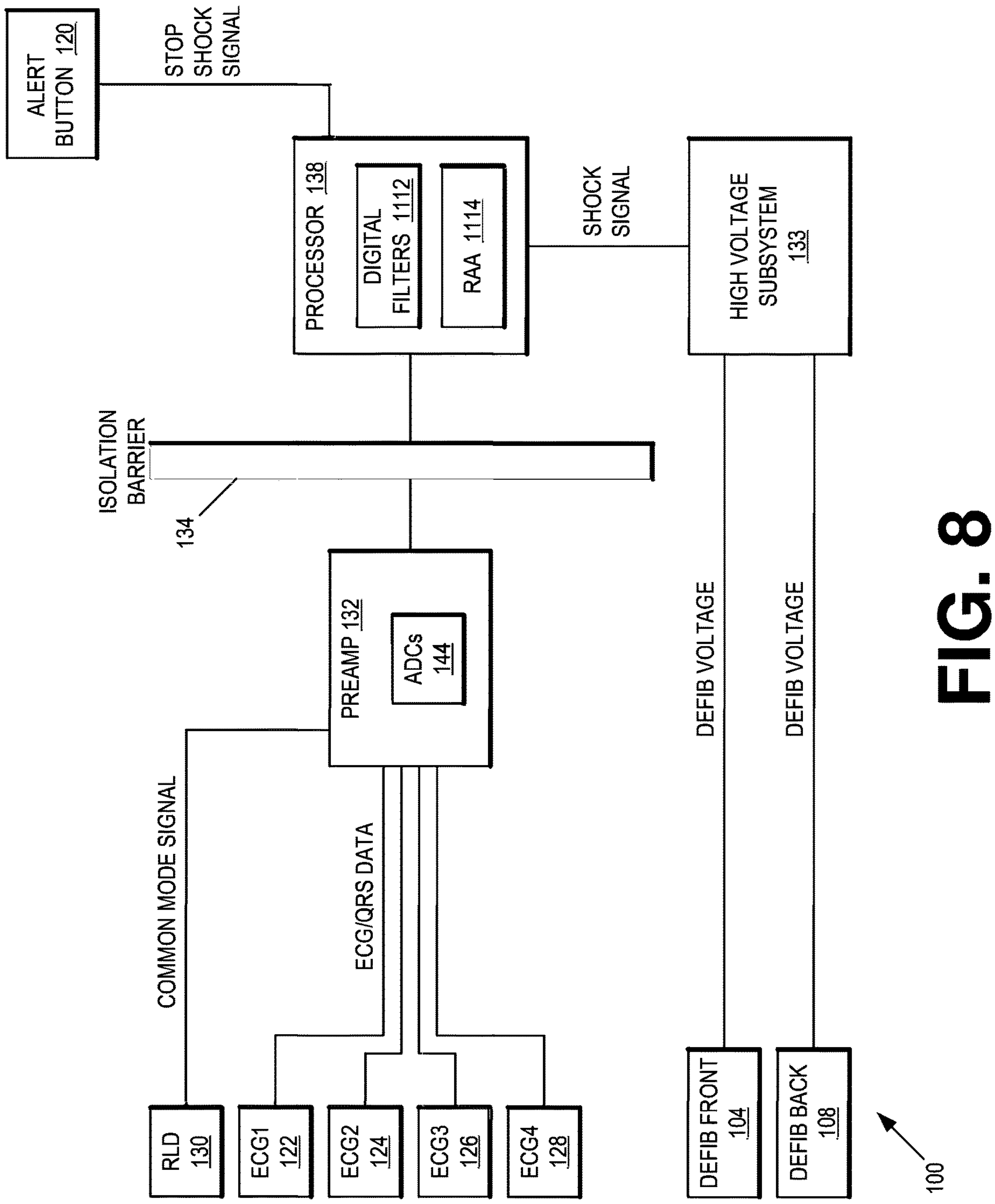
FIG. 8 is a diagram of a WCD system that can operate with a lower false alarm rate in accordance with one or more embodiments.

Referring now to FIG. 8, a diagram of a WCD system that can operate with a lower false alarm rate in accordance with one or more embodiments will be discussed. The WCD system shown in FIG. 8 incorporates one or more of the features discussed herein to enhance ECG and QRS complex signal data detection along with heart rate data detection in order to achieve a lower false alarm rate. The ECG electrodes, ECG1 122, ECG2 124, ECG3 126, and ECG4 128, can comprise silver or silver plated copper electrodes that "dry" attach to the skin of the patient. The ECG electrodes provide ECG/QRS data to preamplifier 132. The preamplifier 132 may have a wide dynamic range at its input, for example +/−1.1 V which is much larger than the amplitude of the ECG signals which are about 1 mV. The preamplifier includes analog-to-digital converters (ADCs) 144 to convert the ECG signals into a digital format. A right-leg drive (RLD) electrode 130 is used to provide a common mode signal so that the ECG signal from the ECG electrodes may be provided to preamplifier 132 as differential signals. The digital ECG signals are provided from the preamplifier 132 eventually to the main processor 138 of monitor 86 via an isolation barrier 134 which operates to electrically isolate the preamplifier 132 and the ECG signals from the rest of the circuity of WCD system.

The processor 138 processes the digital ECG/QRS data received from the preamplifier 132 with one or more digital filters 812. Since the preamplifier 132 has a wide dynamic range that is much wider than the amplitude range of the ECG signals, digital filters 812 may be utilized to process the ECG/QRS data without concern for clipping the incoming signals. One of the digital filters 812 may include a matched filter to facilitate identification of QRS pulses in the incoming data stream. The wide dynamic range of the preamplifier 132 allows at least most of the ECG filtering to happen in software without the signal being clipped. Digital filters 812 can be very effective at removing artifacts from the ECG/QRS data and may contribute to the enhanced false positive performance, that is a lower false positive rate, of the WCD system according to embodiments as described herein.

The processor 138 can apply the rhythm analysis algorithm (RAA) 814 using QRS width information and heart rate data extracted from the digital ECG data using the segment-based processing analysis 600 of FIG. 6 and the QRS width versus heart rate graph 700 of FIG. 7 to make a shock or no-shock determination. The RAA 814 receives the digitized ECG signal and calculates the heart rate and QRS width for each segment. The digitized ECG signal is passed over the isolation barrier 134, and the heart rate is derived from the digitized ECG signal. The heart rate and QRS width are used for making a shock/no-shock decision for each segment, which then can lead to an alarm and a shock. In the event a shockable event is identified, the processor 138 will open a tachycardia episode to start the shock process. Unless the patient provides a patient response using the stop button 120 or user interface 140 to send a stop shock signal to the processor 138 to intervene before the shock is applied, the processor 138 can send a shock signal to the high voltage subsystem 133 which will apply a defibrillation voltage across the defibrillator (DEFIB) front electrode 104 and the defibrillator (DEFIB) back electrode 108 to apply one or more therapeutic shocks until there is no longer any shockable event (VT or VF) or until the energy in the battery 142 is depleted.

In one or more embodiments of the WCD system, the digital filters 812 coupled with the wide dynamic range of the preamplifier 132 of the ECG front end circuitry 400 may allow analysis of signals that otherwise would be clipped in systems with a more limited dynamic range. In addition, the matched filter of the digital filters 812 preferentially highlights complexes similar to the patient's normal rhythm. As a result, artifacts that otherwise may be difficult to discriminate using other methods may be significantly attenuated by the matched filter to result in a lower false alarm rate of the WCD system.

The following examples pertain to further embodiments. Example 1 includes a Wearable Cardioverter Defibrillator (WCD) system for a patient comprising: electrodes; a support structure configured to be worn by the patient so as to maintain at least some of the electrodes capable of contact with a body of the patient; a processor coupled to the electrodes, the processor to store data corresponding to one or more event markers in memory in response to occurrence of an event; one or more sensors to detect one or more parameters, wherein occurrence of the event is to be detected based at least in part on detection of the one or more parameters by the one or more sensors or a signal to be generated by one or more of the electrodes; and a communication device, coupled to the memory, to transmit at least a portion of the stored data to a remote device, wherein a patient condition or a WCD system condition is to be detected based at least in part on analysis of the stored data and/or the transmitted portion of the stored data. Example 2 includes the WCD system of example 1, wherein the processor is to store the event marker data continuously, periodically, or for a select period of time after occurrence of the event. Example 3 includes the WCD system of example 1, wherein machine learning and/or artificial intelligence is to be applied to the portion of the stored data and/or the transmitted portion of the stored data to determine the patient condition or the WCD system condition. Example 4 includes the WCD system of example 1, wherein the remote device is to be accessible by a service personnel, a design personnel, a rescue personnel, a clinician, or a physician. Example 5 includes the WCD system of example 1, wherein the communication device is to receive one or more commands from the remote device to cause a change to an operation of the processor. Example 6 includes the WCD system of example 1, wherein the event marker data is to be analyzed to determine one or more of: whether the patient has a good or poor fit with respect to the WCD system based on combination of electrode behavior, existence of dry skin of the patient based on consideration of a finer level of noise presence, quality of ECG signals or fit of the WCD system based on patient respiration, cause of noise being injected into signals based on accelerometer data, noise floor based on the accelerometer data, system abuse or inappropriate use based on the accelerometer data, activity level based on temperature data, trends or changes in events based on gathered statistics, and hardware or system failure based on device diagnostics data. Example 7 includes the WCD system of example 1, wherein the one or more sensors comprise one or more pressure sensors to detect fit quality of the WCD system. Example 8 includes the WCD system of example 1, wherein the one or more sensors comprise one or more temperature sensors to detect abuse or inappropriate use of the WCD system. Example 9 includes the WCD system of example 1, wherein the event marker data comprises: a time stamp associated with an occurrence time of each of the one or more event markers, an event identifier, patient heart rhythm, patient activity, patient wear statistics, current running state, current running activity, state changes, alert button activity, or overall device status. Example 10 includes the WCD system of example 1, wherein the event marker data comprises event specific information including information relating to one or more of: patient information management, programmable parameter operations, episode operations, arrhythmia detection and normal rhythm detections, defibrillation charging operations, shock delivery operations, system power on, battery information, ECG electrode contact status, defibrillator electrode contact status, self-test/service needed/service required conditions, system connectivity changes, user interface changes/updates/activity including vibration and audio, alarm issuing, alert button activity, software update status, processor speed scaling changes, and operational mode changes. Example 11 includes the WCD system of example 1, wherein the memory comprises a volatile storage device, a non-volatile storage device, or combinations thereof. Example 12 includes the WCD system of example 1, wherein the memory comprises a Secure Digital (SD) memory card. Example 13 includes the WCD system of example 1, wherein the communication device is to communicate with the remote device via wired and/or wireless communication. Example 14 includes the WCD system of example 1, wherein a smartphone is to couple the communication device to a communication network. Example 15 includes the WCD system of example 1, wherein a smartphone is to communicate with the communication device via a Bluetooth™ connection, a Zigbee™ connection, a cellular connection, and/or a WiFi (Wireless Fidelity) connection. Example 16 includes the WCD system of example 1, wherein the communication device is to communicate with the remote device via a smartphone or a different mobile device. Example 17 includes the WCD system of example 1, wherein the remote device comprises one or more of: a smart phone, a tablet, a laptop, a computing device, and a cloud. Example 18 includes the WCD system of example 1, further comprising at least one battery to provide electrical energy to operate the processor, the one or more sensors, the communication device, and the memory while the patient is ambulatory. Example 19 includes the WCD system of example 1, further comprising an energy storage module configured to store an electrical charge to allow for delivery of an electric shock toward a heart of the patient via defibrillator electrodes. Example 20 includes the WCD system of example 1, wherein the processor comprises one or more processor cores.

Example 21 includes one or more non-transitory computer-readable media comprising one or more instructions that when executed on a processor of a wearable cardioverter defibrillator ("WCD") system configure the processor to perform one or more operations to: store data corresponding to one or more event markers in memory in response to occurrence of an event; detect one or more parameters at one or more sensors, wherein occurrence of the event is to be detected based at least in part on detection of the one or more parameters by the one or more sensors or a signal to be generated by one or more of electrodes coupled to a support structure configured to be worn by a patient so as to maintain at least some of the electrodes capable of contact with a body of the patient; and transmit, at a communication device, at least a portion of the stored data to a remote device, wherein a patient condition or a WCD system condition is to be detected based at least in part on analysis of the stored data and/or the transmitted portion of the stored data. Example 22 includes the one or more computer-readable media of example 21, further comprising one or more instructions that when executed on the at least one processor configure the at least one processor to perform one or more operations to cause storage of the event marker data continuously, periodically, or for a select period of time after occurrence of the event. Example 23 includes the one or more computer-readable media of example 21, further comprising one or more instructions that when executed on the at least one processor configure the at least one processor to perform one or more operations to cause application of machine learning and/or artificial intelligence to the portion of the stored data and/or the transmitted portion of the stored data to determine the patient condition or the WCD system condition. Example 24 includes the one or more computer-readable media of example 21, further comprising one or more instructions that when executed on the at least one processor configure the at least one processor to perform one or more operations to cause receipt of one or more commands from the remote device at the communication device to cause a change to an operation of the processor. Example 25 includes the one or more computer-readable media of example 21, wherein the remote device is accessible by a service personnel, a design personnel, a rescue personnel, a clinician, or a physician.

Example 26 includes a method to provide a wearable cardioverter defibrillator ("WCD") system, the method comprising: storing, at a processor, data corresponding to one or more event markers in memory in response to occurrence of an event; detecting one or more parameters at one or more sensors, wherein occurrence of the event is detected based at least in part on detection of the one or more parameters by the one or more sensors or a signal to be generated by one or more of electrodes coupled to a support structure configured worn by a patient so as to maintain at least some of the electrodes capable of contact with a body of the patient; and transmitting, at a communication device, at least a portion of the stored data to a remote device, wherein a patient condition or a WCD system condition is detected based at least in part on analysis of the stored data and/or the transmitted portion of the stored data. Example 27 includes the method of example 26, further comprising storing the event marker data continuously, periodically, or for a select period of time after occurrence of the event. Example 28 includes the method of example 26, further comprising applying machine learning and/or artificial intelligence to the portion of the stored data and/or the transmitted portion of the stored data to determine the patient condition or the WCD system condition. Example 29 includes the method of example 26, further comprising receiving one or more commands from the remote device at the communication device to cause a change to an operation of the processor. Example 30 includes the method of example 26, further comprising wherein the remote device is accessible by a service personnel, a design personnel, a rescue personnel, a clinician, or a physician.

Example 31 includes an apparatus comprising means to perform a method as set forth in any preceding example. Example 32 includes machine-readable storage including machine-readable instructions, when executed, to implement a method or realize an apparatus as set forth in any preceding example.

In the methods described above, each operation can be performed as an affirmative act or operation of doing, or causing to happen, what is written that can take place. Such doing or causing to happen can be by the whole system or device, or just one or more components of it. It will be recognized that the methods and the operations may be implemented in a number of ways, including using systems, devices and implementations described above. In addition, the order of operations is not constrained to what is shown, and different orders may be possible according to different embodiments. Examples of such alternate orderings may include overlapping, interleaved, interrupted, reordered, incremental, preparatory, supplemental, simultaneous, reverse, or other variant orderings, unless context dictates otherwise. Moreover, in certain some embodiments, new operations may be added, or individual operations may be modified or deleted. The added operations can be, for example, from what is mentioned while primarily describing a different system, apparatus, device or method.

A person skilled in the art will be able to practice the present invention in view of this description, which is to be taken as a whole. Details have been included to provide a thorough understanding. In other instances, well-known aspects have not been described, in order to not obscure unnecessarily this description.

Some technologies or techniques described in this document may be known. Even then, however, it does not necessarily follow that it is known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases “constructed to”, “adapted to” and/or “configured to” denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet (“ADS”) of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and sub-combinations of elements, features and acts or operations, which are regarded as novel and non-obvious. The claims also include elements, features and acts or operations that are equivalent to what is explicitly mentioned. Additional claims for other such combinations and sub-combinations may be presented in this or a related document. These claims are intended to encompass within their scope all changes and modifications that are within the true spirit and scope of the subject matter described herein. The terms used herein, including in the claims, are generally intended as “open” terms. For example, the term “including” should be interpreted as “including but not limited to,” the term “having” should be interpreted as “having at least,” etc. If a specific number is ascribed to a claim recitation, this number is a minimum but not a maximum unless stated otherwise. For example, where a claim recites “a” component or “an” item, it means that the claim can have one or more of this component or this item.

In construing the claims of this document, the inventor(s) invoke 35 U.S.C. § 112(f) only when the words “means for” or “steps for” are expressly used in the claims. Accordingly, if these words are not used in a claim, then that claim is not intended to be construed by the inventor(s) in accordance with 35 U.S.C. § 112(f).

In various embodiments, the operations discussed herein, e.g., with reference to FIG. 1 et seq., may be implemented as hardware (e.g., logic circuitry or more generally circuitry or circuit), software, firmware, or combinations thereof, which may be provided as a computer program product, e.g., including a tangible (e.g., non-transitory) machine-readable or computer-readable medium having stored thereon instructions (or software procedures) used to program a computer to perform a process discussed herein. The machine-readable medium may include a storage device such as those discussed with respect to FIG. 1 et seq.

Additionally, such computer-readable media may be downloaded as a computer program product, wherein the program may be transferred from a remote computer (e.g., a server) to a requesting computer (e.g., a client) by way of data signals provided in a carrier wave or other propagation medium via a communication link (e.g., a bus, a modem, or a network connection).

Reference in the specification to "one embodiment" or "an embodiment" means that a particular feature, structure, and/or characteristic described in connection with the embodiment may be included in at least an implementation. The appearances of the phrase "in one embodiment" in various places in the specification may or may not be all referring to the same embodiment.

Also, in the description and claims, the terms "coupled" and "connected," along with their derivatives, may be used. In some embodiments, "connected" may be used to indicate that two or more elements are in direct physical or electrical contact with each other. "Coupled" may mean that two or more elements are in direct physical or electrical contact. However, "coupled" may also mean that two or more elements may not be in direct contact with each other, but may still cooperate or interact with each other.

Thus, although embodiments have been described in language specific to structural features and/or methodological acts, it is to be understood that claimed subject matter may not be limited to the specific features or acts described. Rather, the specific features and acts are disclosed as sample forms of implementing the claimed subject matter.

The invention claimed is:

1. A Wearable Cardioverter Defibrillator (WCD) system for a patient comprising:
   - electrodes;
   - a support structure configured to be worn by the patient so as to maintain at least some of the electrodes in proximity with a body of the patient;
   - one or more processors coupled to the electrodes, the one or more processors to store data corresponding to one or more event markers as stored event marker data in a memory in response to an occurrence of an event, wherein the one or more processors are configured to analyze the stored event marker data to determine a number of alarms that have occurred;
   - one or more sensors to detect one or more parameters, wherein the occurrence of the event is to be detected based at least in part on the detection of the one or more parameters by the one or more sensors or a signal generated by one or more of the electrodes; and
   - a communication device, communicatively coupled to the memory, to transmit at least a portion of the stored event marker data to a remote device, wherein the portion of the stored event marker data is transmitted immediately to the remote device responsive to an emergency event, and is otherwise transmitted periodically or by request,
   - wherein a patient condition or a WCD system condition is to be detected based at least in part on analysis of the stored event marker data and/or the transmitted portion of the stored event marker data,
   - wherein the stored event marker data transmitted to the remote device includes noise data from an electrocardiogram (ECG) signal and respiration data to determine whether the patient has a good or poor fit of the support structure, and
   - wherein the one or more processors are further configured to analyze the stored event marker data to determine whether the patient has the good or poor fit of the support structure based on a combination of two or more of: relative behavior of the electrodes, detection of dry skin of the patient based on detection of a finer level of noise presence, and/or detected quality of ECG signals.

2. The WCD system of claim 1, wherein the one or more processors are configured to store the event marker data continuously.

3. The WCD system of claim 1, wherein the one or more processors are configured to apply machine learning and/or artificial intelligence to the portion of the stored event marker data and/or the transmitted portion of the stored event marker data to determine the patient condition or the WCD system condition.

4. The WCD system of claim 1, wherein the remote device is configured to be accessible by a service personnel, a design personnel, a rescue personnel, a clinician, or a physician.

5. The WCD system of claim 1, wherein the communication device is configured to receive one or more commands from the remote device to cause a change to an operation of the one or more processors.

6. The WCD system of claim 1, wherein the one or more sensors comprise one or more pressure sensors fitted to the support structure to detect fit quality of the support structure with the body of the patient.

7. The WCD system of claim 1, wherein the one or more sensors comprise one or more temperature sensors to detect abuse or inappropriate use of the WCD system.

8. The WCD system of claim 1, wherein the stored event marker data comprises: a time stamp associated with an occurrence time of each of the one or more event markers, an event identifier, patient heart rhythm, patient activity, patient wear statistics, current running state, current running activity, state changes, alert button activity, or overall device status.

9. The WCD system of claim 1, wherein the event marker data comprises event specific information including information relating to one or more of: patient information management, programmable parameter operations, episode operations, arrhythmia detection and normal rhythm detections, defibrillation charging operations, shock delivery operations, system power on, battery information, ECG electrode contact status, defibrillator electrode contact status, self-test/service needed/service required conditions, system connectivity changes, user interface changes/updates/activity including vibration and audio, alarm issuing, alert button activity, software update status, processor speed scaling changes, and operational mode changes.

10. The WCD system of claim 1, wherein a smartphone is configured to communicate with the communication device via a Bluetooth™ connection, a Zigbee™ connection, a cellular connection, and/or a WiFi (Wireless Fidelity) connection.

11. The WCD system of claim 1, wherein the communication device is to communicate with the remote device via a smartphone or a different mobile device.

12. A Wearable Cardioverter Defibrillator (WCD) system for a patient comprising:
   - electrodes;
   - a support structure configured to be worn by the patient so as to maintain at least some of the electrodes in proximity with a body of the patient;
   - one or more processors coupled to the electrodes, the one or more processors to store data corresponding to one or more event markers as stored event marker data in a memory in response to an occurrence of an event, wherein the one or more processors are configured to analyze the stored event marker data to determine a number of alarms that have occurred, wherein an alarm occurs when a rhythm analysis algorithm (RAA) executed by one or more of the processors makes a shock decision based at least in part on an analyzed segment of an electrocardiogram (ECG) signal of the patient;

one or more sensors to detect one or more parameters, wherein the occurrence of the event is to be detected based at least in part on detection of the one or more parameters by the one or more sensors or a signal generated by one or more of the electrodes; and a communication device, coupled to the memory, to transmit at least a portion of the stored event marker data to a remote device, wherein the portion of the stored event marker data is transmitted immediately to the remote device responsive to an emergency event, and is otherwise transmitted periodically or by request;

wherein a patient condition or a WCD system condition is to be detected based at least in part on analysis of the stored event marker data and/or the transmitted portion of the stored event marker data;

wherein the emergency event comprises detection of arrhythmia in the patient, and the stored event marker data transmitted to the remote device includes information indicating the detection of arrythmia in the patient, wherein the stored event marker data transmitted to the remote device further includes noise data from an ECG signal and respiration data to determine whether the patient has a good or poor fit of the support structure, and wherein the one or more processors are further configured to analyze the stored event marker data to determine whether the patient has the good or poor fit of the support structure based on a combination of two or more of: relative behavior of the electrodes, detection of dry skin of the patient based on detection of a finer level of noise presence, and/or detected quality of ECG signals.

13. The WCD system of claim 12, wherein the remote device is configured to be accessible by a service personnel, a design personnel, a rescue personnel, a clinician, or a physician.

14. The WCD system of claim 12, wherein the communication device is configured to receive one or more commands from the remote device to cause a change to an operation of the one or more processors.

15. The WCD system of claim 12, wherein the stored event marker data comprises event specific information including information relating to one or more of: patient information management, programmable parameter operations, episode operations, arrhythmia detection and normal rhythm detections, defibrillation charging operations, shock delivery operations, system power on, battery information, ECG electrode contact status, defibrillator electrode contact status, self-test/service needed/service required conditions, system connectivity changes, user interface changes/updates/activity including vibration and audio, alarm issuing, alert button activity, software update status, processor speed scaling changes, and operational mode changes.

16. The WCD system of claim 1, wherein the one or more processors are further configured to analyze the stored event marker data to determine whether the patient has the good or poor fit of the support structure based on consideration of detection of the finer level of noise present in the ECG signal.

17. The WCD system of claim 1, wherein the one or more sensors include an accelerometer and/or temperature sensor, and wherein the determination of whether the patient has the good or poor fit is further based on one or more of data from the accelerometer being indicative of noise being injected into signals, a noise floor determined using data from the accelerometer, system abuse or inappropriate use detected using data from the accelerometer, activity level determined using data from the temperature sensor, trends or changes in events based on gathered statistics, or hardware or system failure based on device diagnostics data.

* * * * *